(12) United States Patent
Bissler et al.

(10) Patent No.: US 6,780,322 B1
(45) Date of Patent: Aug. 24, 2004

(54) HEMOFILTRATION SYSTEM

(75) Inventors: John J. Bissler, Cincinnati, OH (US); Marios M. Polycarpou, Strovolos (CY); Nat Hemasilpin, Cincinnati, OH (US); Efrain O. Morales, Rochester, NY (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 10/030,011

(22) PCT Filed: Apr. 28, 2000

(86) PCT No.: PCT/US00/11620

§ 371 (c)(1), (2), (4) Date: Jun. 11, 2002

(87) PCT Pub. No.: WO00/66197

PCT Pub. Date: Nov. 9, 2000

Related U.S. Application Data

(60) Provisional application No. 60/131,955, filed on Apr. 30, 1999.

(51) Int. Cl.⁷ .............................................. B01D 61/22
(52) U.S. Cl. ........................... 210/637; 210/86; 210/87; 210/96.2; 210/103; 210/143; 210/321.65; 210/645; 210/739; 210/740; 604/4.01; 604/65; 604/67; 706/47; 706/52
(58) Field of Search ........................... 210/86, 87, 96.2, 210/103, 137, 143, 321.65, 637, 645, 646, 650, 739, 740, 767, 929, 96.1, 621.65; 604/4.01, 5.01, 65, 67, 6.09, 6.01; 706/1, 3, 4, 8, 47, 52; 705/3; 417/36, 43

(56) References Cited

U.S. PATENT DOCUMENTS

| | | |
|---|---|---|
| 4,132,644 A | 1/1979 | Kolberg .................. 210/85 |
| 4,178,240 A | 12/1979 | Pinkerton |
| 4,204,957 A | 5/1980 | Weickhardt ................ 210/98 |

(List continued on next page.)

FOREIGN PATENT DOCUMENTS

| | | |
|---|---|---|
| EP | 300201 | 6/1987 |
| EP | 373455 A1 | 6/1990 |
| EP | 611228 | 2/1993 |
| EP | 373455 B1 | 9/1993 |
| FR | 2397197 | 2/1979 |
| WO | WO 93/06875 | 4/1993 |
| WO | WO 98/50091 | 11/1998 |

OTHER PUBLICATIONS

Cobe Laboratories, Inc., *Centrysystem 3—Precise Ultrafiltration Control*, Cobe Laboratories, Inc., Lakewood, CO, 1987.

T.A. Depner, et al., *Pressure effects on roller pump blood flow during hemodialysis*, American Society for Artificial Internal Organs Transactions, 31:M456–M459, 1990.

(List continued on next page.)

*Primary Examiner*—Joseph Drodge
(74) *Attorney, Agent, or Firm*—Wood, Herron & Evans, L.L.P.

(57) ABSTRACT

A multipurpose hemofiltration system (10) and method are disclosed for the removal of fluid and/or soluble waste from the blood of a patient. The system (10) continuously monitors the flow rates of drained fluid, blood, and infusate. When necessary, the pumping rates of the infusate, drained fluid and blood are adjusted to remove a preselected amount of fluid from the blood in a preselected time period. A supervisory controller (160) can monitor patient parameters, such as heart rate (120) and blood pressure (130), and adjust the pumping rates accordingly. The supervisory controller (160) uses fuzzy logic to make expert decisions, based upon a set of supervisory rules, to control each pumping rate to achieve a desired flow rate and to respond to fault conditions. An adaptive controller (162) corrects temporal variations in the flow rate based upon an adaptive law and a control law.

19 Claims, 12 Drawing Sheets

U.S. PATENT DOCUMENTS

| | | | | |
|---|---|---|---|---|
| 4,324,663 A | | 4/1982 | Hirel et al. | 210/646 |
| 4,370,983 A | * | 2/1983 | Lichtenstein | 600/301 |
| 4,372,846 A | | 2/1983 | Yamagami et al. | 210/86 |
| 4,482,598 A | | 11/1984 | Ishii et al. | 428/195 |
| 4,606,826 A | | 8/1986 | Sano et al. | 210/646 |
| 4,684,460 A | | 8/1987 | Issautier | 210/90 |
| 4,728,433 A | | 3/1988 | Buck et al. | 210/646 |
| 4,767,399 A | | 8/1988 | Bollish | |
| 4,769,132 A | | 9/1988 | Patono | 210/86 |
| 4,844,810 A | | 7/1989 | Richalley et al. | 210/646 |
| 4,889,635 A | | 12/1989 | Chevallet | 210/646 |
| 4,923,598 A | | 5/1990 | Schal | 210/87 |
| 4,980,054 A | | 12/1990 | Lavender | 210/90 |
| 5,200,090 A | | 4/1993 | Ford et al. | 210/739 |
| 5,211,849 A | | 5/1993 | Kitaevich et al. | 210/645 |
| 5,344,568 A | | 9/1994 | Kitaevich et al. | 210/545 |
| 5,503,624 A | * | 4/1996 | Roeher et al. | 604/65 |
| 5,679,245 A | | 10/1997 | Manica | 210/134 |
| 5,762,805 A | | 6/1998 | Truitt et al. | 210/645 |
| 5,776,345 A | | 7/1998 | Truitt et al. | 210/645 |
| 5,857,973 A | | 1/1999 | Ma et al. | 600/441 |
| 5,910,252 A | | 6/1999 | Truitt et al. | 210/645 |
| 5,956,464 A | | 9/1999 | Madni et al. | 395/61 |
| 6,007,491 A | | 12/1999 | Ling et al. | 600/481 |
| 6,200,485 B1 | | 3/2001 | Kitaevich et al. | 210/739 |
| 6,423,022 B1 | * | 7/2002 | Roeher et al. | 604/5.01 |
| 6,471,872 B2 | * | 10/2002 | Kitaevich et al. | 210/739 |

OTHER PUBLICATIONS

S. Dirkes., *How to use the new CVVH renal replacement systems,* American Journal of Nursing, 94(5)67–73, 1994.

D. Drainkov, et al., *An Introduction to Fuzzy Control,* Springer–Verlag, 2nd edition, 1996, Ch. 3, FKBC Design Parameters, pp. 103–144.

E.N. Ellis, et al., *Use of pump–assisted hemofiltration in children with acute renal failure,* Pediatric Nephrology, 11:196–200, 1997.

L.G. Forni, et al. *Continuous hemofiltration in the treatment of acute renal failure,* The New England Journal of Medicine, 336(18):1303–1309, 1997.

Gambro AB, *Hemofiltration in Perspective,* Gambro AB, Lund, Sweden, Oct. 1989.

Gambro AB, *AK 10 System—Operator's manual for hemofiltration—BMM 10–1 and HFM 10–1,* Gambro AB, Lund, Sweden, May 1986.

G.C. Goodwin, et al., *Adaptive Filtering, Prediction and Control,* Prentice Hall, 1984, Chapter 6, pp. 182–207.

L.W. Henderson, et al., *Kinetics of hemodiafiltration, II. Clinical characterization of a new blood cleansing modallty,* 1975. Journal of the American Society of Nephrology, 1997, 8(3):494–508; discussion 494–495, 497–500, Mar. 1997.

L.W. Hendersen, et al. (ed), *Hemofiltration,* Springer–Verlag, New York, 1986, pp. 83–89.

W. Heinrichs, et al., *An automatic system for fluid balance in continuous hemofiltration with very high precision,* intensiv–behandlung, II International Conference on Continuous Hemofiltration, Jahrgang 15, Nov. 3, 1990, p. 110.

G. Hillerström, et al., *Application of repetitive control to a peristaltic pump,* Journal of Dynamic Systems, Measurement and Control, 116:786–789, Dec. 1994.

J.H. Holmes, et al., *Removal of fluid from the patient during hemodialysis,* Department of Medicine, U. of Colorado, Mar. 1969.

International Electrotechnical Commission, *International Standard, Medical Electrical Equipment, Part 2:Particular requirement for safety of haemodialysis equipment,* International Electrotechnical Commission, Geneva, Switzerland, 1989.

P.A. Ioannou, et al., *Robust Adaptive Control,* Prentice Hall, 1996, Ch. 1, pp. 8–12.

R. Johnson Jr., *Lecture 13:Model reference adaptive control,* In Lectures on Adaptive Parameter Estimation, Prentice Hall, 1988, pp. 111–117.

Y. Kitaevich, et al., *Development of a high–precision continuous extracorporeal hemodiafiltration system,* Biomedical Instrumentation & Technology, 27(2):150–156, Mar./Apr. 1993.

L.H. Lowrie., *Renal replacement therapies in pediatric multiorgan dysfunction syndrome,* Pediatric Nephrology (2000), 14:6–12.

M. Nordio, et al., *Projection and simulation results of an adaptive fuzzy control module for blood pressure and blood volume during hemodialysis,* 4535 ASAIO Journal, 40(1994), Jul.–Sep., No. 3, Hagerstown, MD, pp. M686–M690.

N.J. Olsthun, et al., *Ultrafiltarion and backfiltration during hemodialysis,* Artificial Organs, 19(11):1143–1161, 1995.

E.P. Paganini, *Acute continouous renal replacement therapy,* Martinus Nijhoff Publishing, 1986, pp. 91–111.

K.M. Passino, et al., *Fuzzy control: The basics,* In Fuzzy Control, Addison–Wesley, 1998, Ch. 2, pp. 22–73.

W. Pedrycz., *Fuzzy controllers–preliminaries and basic construction,* In Fuzzy Control and Fuzzy Systems, Research Studies Press, Somerset, 2nd edition, 1993, Ch. 4, pp. 22–73.

C. Ronco., *Hemofiltration and hemodiafiltration,* In J.P. Bosch, editor, Hemodialysis: High–Efficiency Treatments, vol. 27 of Contemporary Issues in Nephrology, Churchill Livingstone, New York, 1993, Ch. 9, pp. 119–134.

M. Sagy, et al., *Continuous flow peritoneal dialysis as a method to treat severe anasarca in children with acute respiratory distress syndrome,* Critical Care Medicine, vol. 27, No. 11:2532–2536, 1999.

J. Sands, et al., *Difference between delivered and prescribed blood flow in hemodialysis,* American Society for Artificial Organs Journal, 42:M717–M719, 1996.

Sartorius GmbH, *Hemoprocessor 40020 Operating Instructions,* Sartorius GmBH, Gottengen, Germany, Sep. 1984.

J. Schaeffer, et al., *Lon term performance of hermofilter in continuous hemofiltration,* Nephron, 72:155–158, 1996.

T. Terano, et al., *Automotive speed control,* In Applied Fuzzy Systems, Academic Press, Cambridge, 1989, Ch. 3, pp. 85–93.

K.S. Tsakalis, et al., *Model reference control,* In Linear Time Varying Systems: Control and Adaption, Prentic Hall, 1993. Ch. 4, pp. 90–123.

L.X. Wang., *Fuzzifiers and defuzzifiers,* In A Course in Fuzzy Systems and Control, Prentice Hall, 1997, Ch. 8, pp. 105–117.

S. Ash, *Principles and Practice of Hemodialysis Therapy,* CRC Handbook of Clinical Engineering, vol. 1, B.N. Feinberg and D.G. Fleming, ed., CRC Press, 1980, pp. 177–210.

R. Bellomo, et al., *Use of continous haemodiafiltration: An approach to the management of acute renal failure in the critically ill,* American Journal of Nephrology, 12:240–245, 1992, pp. 241–245.

Hospal, *Hospal Instruction Manual,* BSM 22SC, Rev. A, Mar. 1990, pp. 29–30 & 57.

P. Kramer, *Limitations and pitfalls of continuous arterioverious hemofiltration,* Arteriovenous hemofiltration: A kidney replacement therapy for the intensive care unit, P. Kramer, ed., Springer–Verlag, Berlin, 1985, pp. 206–212.

Sartorius, *Sartorius Hemofilter,* Sartorius GmbH, date unknown.

Sartorius Membranfilter, *Sartorius Hemofilter and Hemoprocessor, A new System for Hemofiltration,* Sartorius–Membranfilter GmbH, date unknown.

G. Tao, et al., *4, Fixed Inverse Compensation: 6. Continuous–Time Adaptive Inverse Control; 7. Discrete–Time Adaptive Inverse Control; 9. Adaptive Inverse Control for Output Nonlinearities.* Adaptive Control of Systems with Actuator and Sensor Nonlinearities, John Wiley & Sons, 1996, Chapters 4, 6, 7 & 9.

* cited by examiner

HEMOFILTRATION SYSTEM

This application is a 371 of PCT/US00/11620, filed Apr. 28, 2000 and claims the benefit of provisional application No. 60/131,955, filed Apr. 30, 1999.

This application is related to patent application Ser. No. 08/814,160, filed Mar. 10, 1997, now U.S. Pat. No. 6,471,872, which is a continuation of patent application Ser. No. 08/478,942, filed Jun. 7, 1995, now abandoned, which is a continuation-in-part application of U.S. patent application Ser. No. 08/299,899, filed Sep. 1, 1994, now abandoned, which is a continuation of patent application Ser. No. 08/062,928, filed May 17, 1993, now U.S. Pat. No. 5,344,568, which is a continuation of patent application Ser. No. 07/775,183, filed Oct. 11, 1991, now U.S. Pat. No. 5,211,849, and claims the benefit of U.S. Provisional Application No. 60/131,955, filed Apr. 30, 1999, each disclosure of which is hereby expressly incorporated by reference herein in its entirety.

GENERAL BACKGROUND OF THE INVENTION

For various reasons, including illness, injury or surgery, patients may require replacement or supplementation of their natural renal function in order to remove excess fluid or fluids containing dissolved waste products from their blood. Several procedures known for this purpose are dialysis, hemodialysis, hemofiltration, hemodiafiltration and ultrafiltration; another related procedure is plasmapheresis. The specific procedure employed depends upon the needs of the particular patient For example, dialysis is used to remove soluble waste and solvent from blood; hemofiltration is used to remove plasma water from blood; hemodiafiltration is used to remove both unwanted solute (soluble waste) and plasma water from blood; ultrafiltration is a species of hemofiltration; and plasmapheresis is used to remove blood plasma by means of a plasmapheresis filter. Because the replacement of renal function may affect nutrition, erythropoiesis, calcium-phosphorus balance and solvent and solute clearance from the patient, it is imperative that there be accurate control of the procedure utilized. The accurate control of the rate of removal of intravascular fluid volume is also important to maintain proper fluid balance in the patient and prevent hypotension.

Various systems have been proposed to monitor and control renal replacement procedures. For example, U.S. Pat. No. 4,132,644 discloses a dialysis system in which the weight of dialyzing liquid in a closed liquid container is indicated by a scale. After the dialyzing liquid flows through the dialyzer, the spent liquid is returned to the same container and the weight is again indicated. Since the container receives the original dialyzing liquid plus ultrafiltrate, the amount of ultrafiltrate removed from the patient is equal to the increase in total weight in the container. This system is not driven by a weight measuring device and does not offer precise control of the amount of liquids used in the procedure.

U.S. Pat. No. 4,204,957 discloses an artificial kidney system which utilizes weight measurement to control the supply of substitute fluid to a patient In this system, the patient's blood is pumped through a filter and the filtrate from the blood is discharged to a measuring vessel associated with a weighing device. A second measuring vessel containing substitute fluid is associated with a second weighing device and is connected to the purified blood line. By means of a pump, the substitute fluid and the purified blood are pumped back to the patient. The first and second weighing devices are coupled to one another by a measuring system in such a way that a fixed proportion of substitute is supplied to the purified blood stream from the second measuring vessel depending an the weight of the filtrate received in the first measuring vessel. This system does not utilize circulating dialysate fluid in the blood filtration.

U.S. Pat. No. 4,767,399 discloses a system for performing continuous arteriovenous hemofiltration (CAVH). The disclosed system relies upon utilizing a volumetric pump to withdraw a desired amount of fluid from the patient's blood and return a selected amount of fluid volume to the patient U.S. Pat. No. 4,923,598 discloses an apparatus for hemodialysis and hemofiltration which comprises an extracorporeal blood circuit including a dialyzer and/or filter arrangement. The system determines fluid withdrawal per unit time and total amount of fluid withdrawn by utilizing flow sensors in conjunction with an evaluating unit located upstream and downstream of the dialyzer or filter arrangement in the blood circuit.

U.S. Pat. No. 4,728,433 discloses a system for regulating ultrafiltration by differential weighing. The system includes a differential weighing receptacle having an inlet chamber and an outlet chamber which allows a fixed amount of fresh dialysate, by weight, to flow through the hemodialyzer. This system operates in a sequence of weighing cycles during which the amount of ultrafiltrate removed from the blood may be calculated. Additionally, the ultrafiltration rate for each weighing cycle may be calculated. This system provides a mechanism for determining and regulating the amount of ultrafiltrate removed from the blood while delivering dialysate to the patient in alternating fill and drain cycles of the inlet and outlet chambers of the differential weighing receptacle.

For certain patients, renal replacement procedures may extend over hours or even days. In general current systems for monitoring and controlling renal replacement procedures lack the flexibility and accuracy required to perform such procedures on neonates. This is mainly due to the absence of a satisfactory automatic control of the pumps employed. Because of the patient risk involved in using such equipment, health care personnel measure the fluid removed from the patient on an hourly basis. The continuing need to monitor the fluid removed leads to a significant increase in nursing care and thus increases the cost of the therapy. Therefore, there is a need to improve the level of autonomy for the systems such that the procedure is less time consuming for medical personnel, and consequently less costly. However, the enhanced autonomy must not come at the expense of patient safety.

Some conventional renal function replacement/supplementation systems possess an elementary level of supervisory control that simply detects the presence of a fault condition, sounds an alarm, and de-energizes the system pumps to halt the procedure. If the hemofilter clots while the pumps are de-energized, the tubing and hemofilter must be replaced with a concomitant increase in the chance of infection for the patient. Furthermore, the hemofiltration procedure is delayed with a possibly negative impact upon the patient's health.

Due to the time-varying nature of the renal function replacement/supplementation system, the dynamics of fluid pumping may change over time. For example, the characteristics of system components such as tubing, filter, and connectors may vary slowly over time due to aging or as occlusion of the path for fluid flow. As the flow path becomes constricted, the pumping rate of the pump must be altered to compensate for the increased flow resistance. Furthermore, the replacement of a tubing set requires a rapid change adjustment of the pumping rates that may be difficult to initially establish as a relatively constant value due to short-term transient variations. Current systems for monitoring and controlling renal replacement procedures lack the ability to autonomously correct these time-dependent flow rate variations with high accuracy, rapid response, and minimal overshoot or transient variations following correction.

The need exists for a multipurpose renal function replacement/supplementation system which is accurate, reliable, capable of continuous, long-tern operation, and which can be used effectively on adult, pediatric and neonatal patients. Further, the need exists for a feedback control system for controlling the multipurpose renal function replacement/supplementation system that accurately regulates the transfer of fluid and monitors the overall behavior of the system to improve patient care and provide greater autonomy.

GENERAL SUMMARY OF THE INVENTION

The present invention is directed to a multipurpose system and method for removal of fluid and/or soluble waste from the blood of a patient: ultrafiltration only, hemodiafiltration, hemodiafiltration and ultrafiltration, hemodialysis, and plasmapheresis with or without fluid replacement. The system and method of the present invention can provide reliable, long term operation (5–10 days) with a great degree of accuracy (on the order of ±2 grams regardless of the total volume of fluid passing through the system). The system and method of the invention are advantageous because of the multipurpose nature thereof, the repeatability and accuracy of the processes, and the simultaneous, continuous flow of fluids in an extracorporeal blood circuit, while being equally applicable to adult, pediatric and neonatal patients.

As used herein the term "hemofiltration" is to be broadly construed to include hemodialysis, hemofiltration, hemodiafiltration, ultrafiltration and plasmapheresis processes. As used herein, the term "infusate" is defined to include dialysate fluid or any other replacement fluids which may be supplied to the patient as a part of the hemofiltration procedures.

In a preferred embodiment, the system of the present invention includes a hemofilter, a blood pump for pumping blood from a patient through the hemofilter and back to the patient, and suitable tubing for carrying the pumped blood to and from the patent. The system further includes a first reservoir for maintaining a supply of infusate, a first weighing means for continuously monitoring the weight of the infusate and generating weight data signals correlated to the monitored weight, and a first pump for pumping the infusate from the first reservoir to the hemofilter or appropriate blood tubing access port. A second reservoir receives drained fluid (e.g., spent infusate or ultrafiltrate, including the fluids and solutes removed from the blood) from the hemofilter, and a second weighing means monitors the weight of the drained fluid and generates weight data signals correlated to the monitored weight. A second pump pumps the drained fluid from the hemofilter to the second reservoir. The system also includes a computerized controller operably connected to the blood pump, the infusate pump, the drain pump and the first and second weighing means.

The controller periodically, but on an ongoing basis during the treatment, interrogates at predetermined intervals the weight data signals that are continuously generated by the first and second weighing means and is designed to determine therefrom the weight of infusate and drained fluid in the first and second reservoirs at the predetermined intervals. The rate of fluid withdrawal from the blood is also determined. The controller compares the infusate and drained fluid weights to corresponding predetermined computed weights in the memory of the controller, and, when necessary, the controller generates control signals which automatically adjust the pumping rates of the infusate and drained fluid pumps in order to achieve a preselected amount of fluid removal from the patient's blood. Additionally, the controller is programmed to operate the infusate and drained fluid pumps only when the blood pump is operating. Furthermore, the blood pump is operably connected to and is responsive to control signals generated by the controller in response to or independent of the weight data signals to vary the flow rate of the blood through the hemofilter as required to achieve the desired level of fluid removal from the blood.

In an alternative embodiment, the computer controller is, by initial selection of the operator, interfaced with one or more of the various monitoring systems that are operably connected to the patient. These monitoring systems, which are well known in the art, generate and output data signals corresponding to the monitored patient parameters, and the computer controller receives such data signals. During the hemofiltration operation, the interfaced parameters are constantly monitored; however, the controller only responds to specific parameter data that corresponds to the patient parameters selected by the operator. The patient parameters which may be monitored and interfaced with the computer controller include the following: arterial pressure, central venous pressure, pulmonary arterial pressure, mean arterial pressure, capillary wedge pressure, systemic vascular resistance, cardiac output, $O_2$ and $CO_2$ content and saturation (expired, venous or arterial), blood pressure, heart rate, patient weight, external infusion rates, and hematocrit. Numerous of these parameters may be monitored and corresponding output data signals generated in known manner utilizing an indwelling intravenous or intra-arterial catheter. The remaining parameters are monitored and data signals are generated by means well known in the art. The operator will select one or more of the above parameters to interface with the controller which will then periodically, but on an ongoing basis during treatment, interrogate at predetermined intervals the parameter data signals that are continuously generated by the interfaced monitoring system(s). The controller then evaluates the parameter data and in response thereto, when necessary, the controller generates control signals which automatically adjust the pumping rates of the infusate, drained fluid and blood pumps so as to achieve a preselected amount of fluid removal from the patient's blood for patient benefit and safety.

It will be appreciated that the system of the present invention may utilize a combination of monitoring and responding to the infusate and drained fluid weight data signals, as described in connection with the first embodiment hereinabove, along with one or more of the other patient parameters interfaced to the controller.

By way of specific examples, in connection with monitoring the patient's weight, the computer controller may be interfaced with a bed scale which provides continuous values for the patient's weight In response to the overall patient weight data signals, the computer controller may control the infusate and/or drained fluid pumps to achieve a predesigned protocol for decreasing or increasing the patient's weight over time. The increase or decrease in patient's weight can be accomplished in either a linear or non-linear manner with respect to time by appropriate pump control. Similarly, the computer may be interfaced with a continuous read-out device of the patient's $O_2$ saturation and the controller will receive, evaluate and respond to the $O_2$ saturation data by controlling the infusate, drained fluid and blood pumping rates accordingly to optimize patient oxygenation.

In connection with all of the above-described monitored parameters, the computer controller will receive data signals corresponding and relating to each particular selected parameter from an appropriate signal generating device or source operably connected to the patient. The controller will then, after periodic interrogation, compare the interrogated values with predetermined desired values and will automatically make the appropriate, predetermined changes in the infusate, drained fluid and blood pumping rates in response to the monitored signals. Furthermore, more than one of the above-referenced parameters can be continuously monitored simultaneously and the computer may be programmed with a hierarchy to consider one or more specific parameters rather than others and will respond with the appropriate and desired adjustments in infusate, drained fluid and blood pumping rates based on those selected parameters.

The computer controller is designed and programmed to adjust the pumping rates (pump speed) of the infusate, drained fluid and blood pumps so as to provide a linear response or a non-linear (curvilinear) response to the observed changes in the selected monitored parameters. In this regard, "linear" is defined to mean a fixed, non-exponential change, and "non-linear" or "curvilinear" means anything other than linear. The selection of linear versus non-linear response profile is made by the operator of the system depending on the needs of the patient. For example, in certain situations it may be desirable to have an initially fast fluid removal rate that decreases over time. In that case a curvilinear or exponential response would be utilized. In other circumstances, consistent or constant fluid removal over time is desired, and so a linear response profile is selected. It is further contemplated that at the election of the operator the computer controller may combine linear and curvilinear response signals so as to tailor the pump rates to achieve a desired response profile. For example, a non-linear initial response period for fast initial fluid removal, followed by a linear response period for ongoing fluid removal at a consistent rate.

In yet another alternative embodiment, the computer controller receives data signals from one or more patient infusion pumps that are otherwise independent of the hemofiltration system. These infusion pumps are used for infusion to the patient of intravenous fluids, medications, parenteral nutrition and/or blood products. By monitoring the data output from the independent infusion pumps, the extraneous total fluid volume per unit time may be ascertained. The controller will then, as required, change the pumping rates of the system infusate, drained fluid and blood pumps, as necessary, so as to alter the ultrafiltration rate and/or infusate fluid rate automatically in response to changes in intravenous fluid therapy. This facilitates independent patient management while hemofiltration is being performed. Proper coordination of the controller with the independent infusion pumps allows the desired or targeted fluid removal goals by hemofiltration to be achieved automatically in concordance with ongoing intravenous fluid therapy.

In an additional alternative embodiment, the computer controller incorporates a supervisory control system operably connected to one or more of the system infusate, drained fluid and blood pumps for controlling the pumping rates of the respective fluids. The supervisory controller receives and utilizes feedback data signals, correlated with the fluid flow rates, regarding the pumping rate of the blood pump that is provided by a flowmeter and the pumping rate of the infusate and drained fluid pumps from the rate change in weight data signals that is provided by electronic scales. The supervisory controller also receives and utilizes patient parameters derived from patient parameter monitors, such as blood pressure data signals from a blood pressure monitor or heart rate data signals from a heart rate monitor. The supervisory controller analyzes these signals utilizing fuzzy logic, based on at least one predetermined supervisory rule, and furnishes an output signal to the appropriate pump to adjust, as necessary on a periodic ongoing basis, the flow rate of fluid generated by that pump. For example, a set of supervisory rules may decide, based upon whether the heart rate and blood pressure are high, normal, or low, to increase or decrease the ultrafiltration rate, or even to discontinue the procedure due to a fault condition.

In yet an additional alternative embodiment, the computer controller incorporates an adaptive control system for controlling the pumping rate of at least one of the system infusate, drained fluid and blood pumps. The adaptive controller is operably connected to each pump to be adaptively controlled and to its associated flow rate sensor. The adaptive control system receives flow rate data signals correlated to the fluid flow rate from a sensor, such as a flowmeter or weight scale, measuring the flow rate of fluid generated by the pump being controlled. The adaptive controller calculates a controller parameter vector using an adaptive law to generate a set of controller parameters for correcting time-dependent deviations of the flow rate from a predetermined flow rate. Based on the controller parameters, the adaptive controller then uses a control law to generate an output signal for adjusting the pumping rate of fluid generated by the pump to achieve the predetermined flow rate. Finally, the controller provides the output signal to the pump on a periodic ongoing basis for adjusting the fluid flow rate. In one aspect, the adaptive controller may use parameter projections to limit the range of the output signal for maintaining the pump in a linear regime of pump operation.

In a preferred embodiment of the method of the present invention, blood from a patient is pumped through a hemofilter and a supply of infusate, which is maintained in a first reservoir, is pumped from the first reservoir through the hemofilter, countercurrent to the blood. The weight of infusate in the first reservoir is continuously monitored and data signals correlated to that weight are generated. Drained fluid (e.g., spent infusate) is pumped from the hemofilter and is received in a second reservoir. The weight of the drained fluid in the second reservoir is continuously monitored and weight data signals correlated thereto are generated. The signals correlated to the weight of infusate and drained fluid are interrogated at regular intervals (for example every minute) by a system controller and are compared to corresponding predetermined computed weights in the memory of the controller. The controller determines the amount and rate of fluid withdrawal from the patient's blood. If those values differ from preselected, preprogrammed desired values, the controller generates control signals which independently adjust the pumping rates of the infusate and drained fluid pumps so as to achieve the desired amount of fluid removal. The control signals may also control the blood pumping rate.

In an alternative embodiment of the method of the present invention, independent of or in addition to the infusate and drained fluid weight monitoring and pump control, the computer controller may be interfaced with one or more of the previously discussed monitoring systems. In this embodiment, the controller will receive, evaluate and respond to the selected patient parameter data by generating appropriate, responsive control signals by which the infusate, drained fluid and blood pumping rates are controlled to achieve the desired amount of fluid removal. This may be accomplished in combination with or independent of the infusate and drained fluid weight monitoring.

In an alternative embodiment of the method of the present invention, flow rate data signals for the fluid flow generated by a pump in a hemofiltration system and patient parameter data signals, such as heart rate and blood pressure, are supplied to a supervisory controller. Flow rate data signals are derived from the rate change in weight of either infusate or drained fluid or from the blood flow rate. The signals are analyzed utilizing fuzzy logic based on at least one predetermined supervisory rule and an output signal is provided to the appropriate pump to adjust, as necessary on a periodic ongoing basis, the flow rate of fluid generated by that pump.

In yet another alternative embodiment of the method of the present invention, flow rate data signals for the fluid flow generated by a pump in a hemofiltration system are supplied to an adaptive controller. Flow rate data signals are derived from the rate change in weight of either infusate or drained fluid or from the blood flow rate. A set of controller parameters is generated from the flow rate signals for use in correcting time-dependent deviations in flow rate from a predetermined flow rate. The signals and parameters are analyzed using a control law to generate an output signal. The output signal is provided to the adaptively controlled pump on a periodic ongoing basis.

The advantages of the system and method of the present invention are achieved at least in part due to the continuous monitoring and periodic interrogation of the fluid weights, and other selected patient parameters, and the adjustment of fluid pumping rates in response thereto, including the blood pumping rate, so as to achieve ideal or nearly ideal fluid removal and replacement if necessary from a patient's blood. Further, the supervisory system controller and adaptive system controller implement closed-loop, feedback control systems that precisely and accurately adjust and control the pumping rates. Further features and advantages of the system and apparatus of the present invention will become apparent with reference to the Figure and the detailed description which follows.

DETAILED DESCRIPTION OF THE INVENTION

Figure 1:
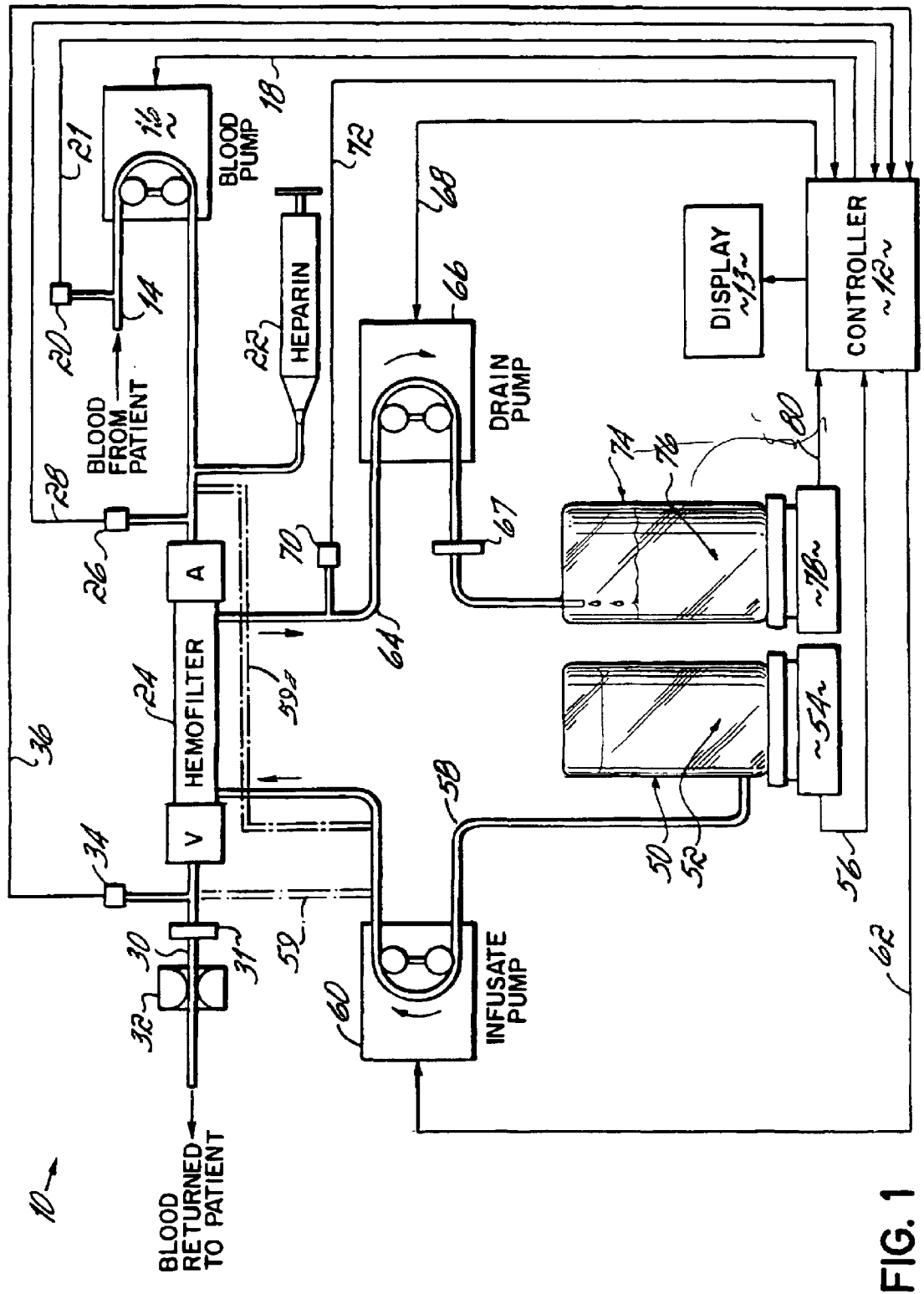
FIG. 1 is a diagrammatic representation of one embodiment of the system of the present invention; a variation is shown in phantom.

FIG. 1 shows a diagrammatic representation of a preferred embodiment of the system of the present invention. The portion of FIG. 1 shown in phantom represents an alternative embodiment of the present invention which will be described hereinbelow. Hemofiltration system 10 is operated and controlled by a suitable controller designated generally as 12. Controller 12 may be a programmable computer having a display 13 and is operably connected to various components of hemofiltration system 10, as will be described in greater detail hereinafter.

In operation, blood is pumped from a patient (not shown), which may be an adult, pediatric or neonatal patient, through a suitable catheter (not shown) and input tubing 14 by means of a blood pump 16. Blood pump 16, which is preferably of the roller type, is operably connected to controller 12 by line 18. One suitable blood pump is the RS-7800 Minipump manufactured by Renal Systems, Minneapolis, Minn. Input tubing 14 through which the patient's blood is pumped preferably includes a pressure transducer 20 upstream of pump 16. Pressure transducer 20 is operably connected to controller 12 via line 21. Means are included downstream of blood pump 16 for accessing input tubing 14 to enable the injection or infusion of desired fluids, including medications and anticlotting compounds such as heparin, into the patient's blood. The injection or infusion of such fluids to the blood may be accomplished in any suitable manner; FIG. 1 shows diagrammatically a syringe and tube arrangement 22, but it will be appreciated that other means could be employed for the same purpose.

The patient's blood is pumped through hemofilter 24 by blood pump 16. Filters of the type suitable for use in the system of the present invention are readily available; one example of a suitable hemofilter is the Diafilter manufactured by AMICON, Denvers, Mass. Where the present system is used to perform plasmapheresis, a suitable plasmapheresis filter such as the Plasmaflo manufactured by Parker Hannifin, Irvine, Calif. can be employed.

Input tubing 14 includes a second pressure transducer 26 slightly upstream of hemofilter 24. Pressure transducer 26 is operably connected to controller 12 via line 28. The patient's blood exits hemofilter 24, passes through output tubing 30 and is returned to the patient via any suitable means such as a venous catheter arrangement (not shown). Output tubing 30 preferably includes a suitable blood flow detector 31 which verifies that there is blood flow in the system and an air bubble/foam control device such as air bubble clamp 32 to prevent the passage of air bubbles to the patient. Blood flow detector 31 and air bubble clamp 32 may be operably connected (not shown) to controller 12 or directly to the pumps to interlock all pumps upon detection of any air bubbles in the blood or upon the cessation of blood flow. A suitable foam-bubble detector is the RS-3220A manufactured by Renal Systems. Output tubing 30 also preferably includes a pressure transducer 34 immediately downstream of hemofilter 24. Pressure transducer 34 is operably connected to controller 12 via line 36.

A first reservoir 50 maintains a supply of suitable dialysate or other fluid, referred to herein generally as infusate 52. The infusate-containing reservoir 50 is supported by a weighing device such as electronic scale 54 which is operably connected to controller 12 via line 56. Infusate 52 is pumped from reservoir 50 via tubing 58 by means of infusate pump 60, which is preferably of the roller variety. A suitable pump for this purpose is a 3½" Roller Pump manufactured by PEMCO, Cleveland, Ohio. Infusate pump 60 is operably connected to controller 12 via line 62 and pumps infusate 52 through hemofilter 24 countercurrent to the blood pumped therethrough. In accordance with known principles, infusate 52 may extract certain components (fluids and/or soluble waste) from the blood passing through hemofilter 24. The fluid drained from hemofilter 24 includes spent infusate and the components removed from the blood, which are refereed to herein as drained fluid 76. In an alternative embodiment wherein system 10 is used as a fluid or plasma replacement system, e.g., to perform plasmapheresis, the infusate (which may be blood plasma) from reservoir 50 is pumped via tubing 59 (shown in phantom) to blood output tubing 30 or via tubing 59a (also shown in phantom) to input tubing 14, thereby replacing the fluid volume removed from the blood. In this embodiment, the drained fluid 76 from hemofilter or plasmapheresis filter 24 does not include any spent infusate since the infusate is pumped directly to blood output tubing 30 or input tubing 14 and supplied to the patient.

The drained fluid 76 is pumped from hemofilter 24 through outlet tubing 64 by means of drain pump 66, which is preferably a roller-type pump, and may be the same as infusate pump 60. Drain pump 66 is operably connected to controller 12 via line 68. Output tubing 64 preferably includes a pressure transducer 70 downstream of hemofilter 24, but upstream of drain pump 66. Pressure transducer 70 is operably connected to controller 12 via line 72. Output tubing 64 also preferably includes a blood leak detector 67 which detects the presence of blood in the drained fluid 76, as may occur if hemofilter 24 ruptures. A suitable blood leak detector is sold by COBE, Lakewood, Colo. as model 500247000. Blood leak detector 67 may be operably connected (not shown) to controller 12 or directly to the pumps to interlock all pumps upon the detection of blood in the drained fluid. Drained fluid 76 pumped from hemofilter 24 is pumped into a second reservoir 74 which collects the drained fluid. Second reservoir 74 is supported by a weighing device such as electronic scale 78, which is operably connected to controller 12 via line 80.

Scales 54 and 78, which may be model 140 CP sold by SETRA of Acton, Mass. continuously generate weight data signals correlated to the weight of infusate and drained fluid contained in reservoirs 50 and 74, respectively. Those weight data signals are continuously fed to controller 12, to which the scales are linked through an interface having a data protocol, such as an RS-232 interface. It will be appreciated that a single scale could be utilized in place of the two scales whereby the weight differential between reservoir 50 and 74 is monitored and a corresponding data signal is generated. Pressure transducers 20, 26, 34 and 70 all continuously measure the pressure at their respective locations in hemofiltration system 10 and generate pressure data signals correlated thereto which are fed to controller 12. A suitable type of pressure transducer is model number 042-904-10 sold by COBE of Lakewood, Colo. When certain predetermined alarm or danger conditions exist in the system 10, as represented by the pressure data signals, the controller will either adjust the infusate, drained fluid, or blood pumping rate, or a combination thereof, or will shut the system down entirely.

Controller 12 is preferably a programmable computer that is capable of sending and receiving signals from auxiliary equipment including pressure transducers 20, 26, 34 and 70, first and second scales 54 and 78, respectively, and blood pump 16, infusate pump 60, and drain pump 66. In operation, controller 12 interrogates, at regular intervals, the weight data signals generated by first and second scales 54 and 78. From these signals, controller 12 determines the weight of infusate and drained fluid in the first and second reservoirs 50 and 74 at that point in time, and compares those weights to corresponding predetermined computed weights which have been programmed into and are stored by controller 12. By monitoring the weight of infusate in reservoir 50 and the weight of drained fluid in reservoir 74 at regular intervals, the rate of change of those weights and the rate of hemofiltration can be calculated by the computer portion of controller 12. When the weights deviate from the predetermined computed weights and/or the rate of hemofiltration deviates from a preselected, preprogrammed desired rate, controller 12 generates control signals which control or adjust the rates at which blood pump 16, infusate pump 60 and drain pump 66 are operated, as necessary, to adjust the hemofiltration rate to the desired rate, or to stop the pumps when preselected limits have been reached. This is accomplished in a continuous manner, i.e., continuous weight data signal generation, periodic interrogation of those weight data signals and computation of the required weight and/or rate information, comparison to predetermined computed values and automatic adjustment of the pumping rates of the pumps, as necessary, to achieve the desired amount and/or rate of hemofiltration.

Controller 12 is programmed so that infusate pump 60 and drain pump 66 are operated only when blood pump 16 is being operated. In the case when ultrafiltration is being performed, the pumping rate of drain pump 66 must equal the pumping rate of infusate pump 60 plus the desired ultrafiltration rate.

Controller 12 continuously receives pressure data signals from pressure transducers 20, 26, 34 and 70 and is programmed to generate alarm signals when high and low pressure limits are exceeded at any of the monitored locations. Furthermore, an alarm signal is generated when the pressure differential across hemofilter 24 exceeds a predetermined upper limit, as monitored specifically by pressure transducers 26, 34 and 70. Additionally, controller 12 may stop the pumps when preselected pressure limits (high or low) are exceeded, as for example may occur if the system tubing becomes occluded or ruptures or if pump occlusion occurs. Finally, controller 12 may signal when the infusate level in reservoir 50 reaches a predetermined lower limit and when the drained fluid level in reservoir 76 reaches a predetermined upper limit. Hemofiltration system 10 may also include suitable blood warmer and infusate warmer devices (not shown) to adjust and/or maintain the blood and infusate temperatures at desired levels. Such devices may also generate alarm signals when the fluid temperatures are outside of preselected limits.

Display 13 offers updated display of measured and computed parameters such as pressures, pressure differentials, temperatures, flow rates and amounts of infusate, drain and ultrafiltration, and alarm conditions. Controller 12 generates both visual and audible alarms and all the pumps are interlocked to prevent operation thereof under alarm conditions. Users have the option of disabling or unabling the alarms (the audible part of the alarm and its interlock with the pumps) to perform a procedure under close supervision. A printer (not shown) is operably connected (not shown) to controller 12 to generate a hard copy of procedural data currently displayed or stored at regular intervals, at the completion of a procedure or at any desired time.

Hemofiltration system 10 can be operated in one of two modes: 1) a manual mode wherein the pumping rates of blood pump 16, infusate pump 60 and drain pump 66 are provided by controller 12 when fixed voltages are applied; and 2) an automatic mode wherein the pumps are controlled by controller 12 when the desired hemofiltration amount or rate has been programmed into the controller. The automatic mode allows the system to be paused and later continued without losing previously measured and computed data.

Figure 2:
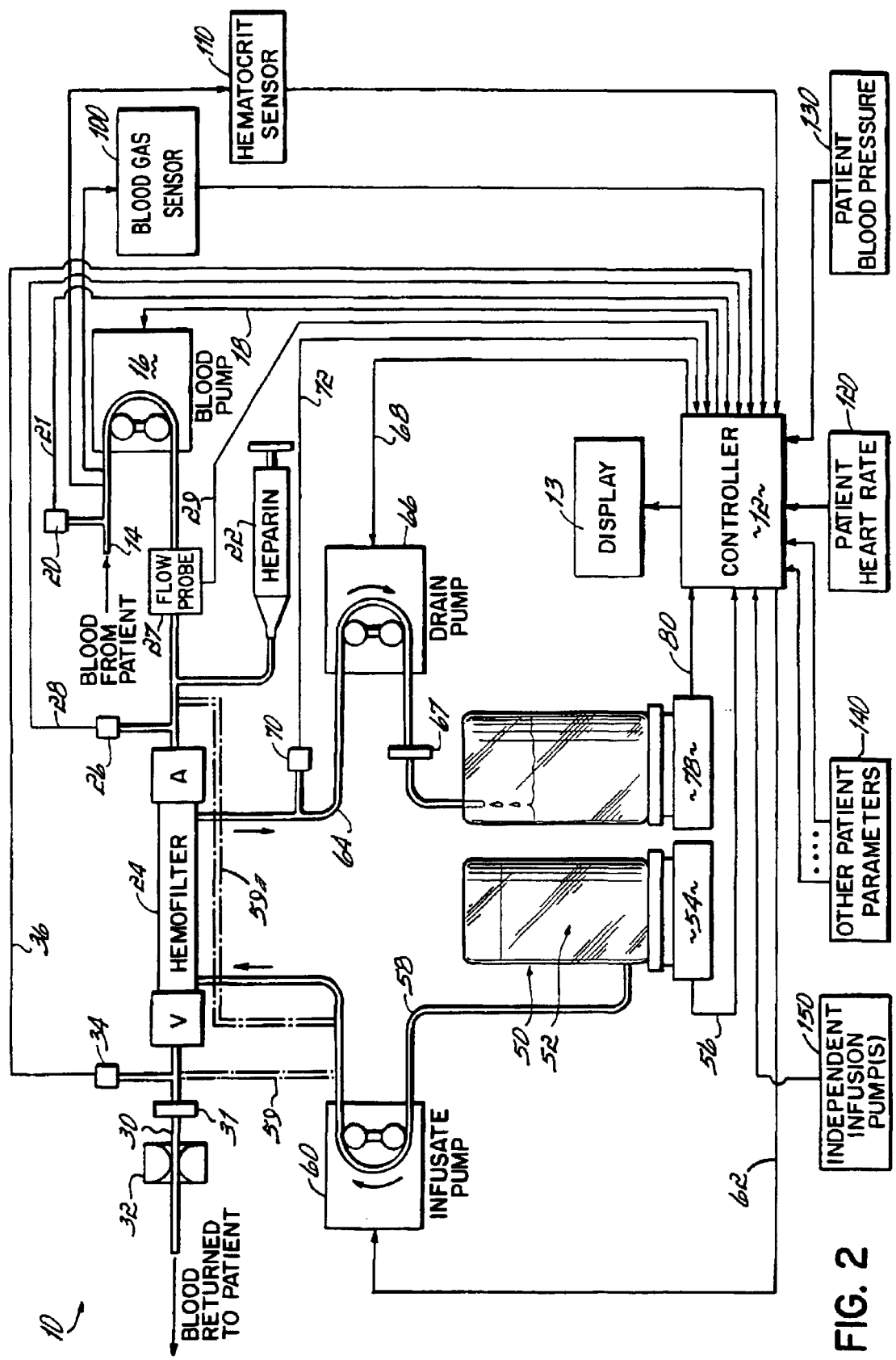
FIG. 2 is a diagrammatic representation of an alternative embodiment of the system of the present invention.

FIG. 2 shows a diagrammatic representation of several alternative embodiments of the hemofiltration system 10 of the present invention. Because of the commnonality of many of the system components in FIG. 2 vis-a-vis the system depicted in FIG. 1, like reference numerals are intended to indicate like components. Furthermore, the system components in FIG. 2 operate in the same manner as the corresponding system components shown in FIG. 1 and described hereinabove. Input tubing 14 further includes a flowmeter or flow probe 27 slightly upstream of hemofilter 24. The flow probe 27 is operably connected to controller 12 via line 29. A suitable flow probe 27 is an ultrasonic flow probe manufactured by Transonic Systems, Inc. Other suitable types of flowmeters include a bearingless rotary flowmeter, a Doppler flowmeter, and a differential electromagnetic flowmeter.

The hemofiltration system of FIG. 2 further includes interfaces between controller 12 and monitoring systems which generate parameter data signals corresponding to selected patient parameters such as blood gas 100, hematocrit 110, patient heart rate 120, patient blood pressure 130 and numerous other patient parameters (designated generally as 140), which other parameters may be one or more of the following: arterial pressure, central venous pressure, pulmonary arterial pressure, mean arterial pressure, capillary wedge pressure, systemic vascular resistance, cardiac output, end tidal $O_2$ and $CO_2$, core and peripheral body temperature, and patient weight. While the blood gas sensor 100 and hematocrit sensor 110 are shown as being connected to the input tubing 14, these parameters can also be monitored by means associated directly with the patient rather than via tubing 14. In fact, whereas venous $O_2$ saturation could be measured as indicated, arterial $O_2$ saturation would require the monitor to be located elsewhere. The overall patient weight parameter can be monitored utilizing a standard patient bed scale (not shown) as is well known in the art.

During the hemofiltration procedure, one or more of the various patient parameters will be monitored continuously and the controller will, at the selection of the operator, be responsive to selected parameter data supplied to the controller. The parameter data may be evaluated and responded to by the controller independent of the infusate and drained fluid weight data signals; i.e., the system may operate and respond based on one or more of the selected parameters and not the weight data signals; or the system may respond to a combination of the weight data signals and one or more selected specific parameters.

One or more independent patient infusion pumps 150 may be interfaced with computer controller 12 to supply data signals correlated to the infusion to the patient of intravenous fluids, medications, parenteral nutrition and/or blood products. The controller 12 may evaluate this data and make modifications to the infusate, drained fluid and blood pumping rates so as to compensate for the extraneous fluid being delivered to the patient by means of the infusion pumps. In this regard, the overall fluid balance in the patient can be managed concurrent with the hemofiltration procedure.

In an alternative embodiment wherein system 10 is used to perform an ultrafiltration procedure or hemodialysis procedure, the infusate (which may be one or more replacement fluids such as a calcium replacement fluid or a bicarbonate replacement fluid) from reservoir 50 is pumped via tubing 59 (shown in phantom) to blood outlet tubing 30 or via tubing 59a (also shown in phantom) to input tubing 14, thereby offsetting substances and fluid volume removed from the blood. In this embodiment, the drained fluid 76 from hemofilter 24 does not include any spent infusate since the infusate is pumped directly to blood output tubing 30 and supplied to the patient. In yet another alternative embodiment, a distinct replacement fluid may be provided by a system having more than one infusate pump 60. For example, infusate pump 60 may be a first infusate pump for delivering a first replacement fluid to blood outlet tubing 30 via tubing 59 and the system 10 may further include a second infusate pump (not shown) for delivering a second replacement fluid to blood outlet tubing 30 via a length of tubing (not shown but similar to tubing 59).

Figure 3:
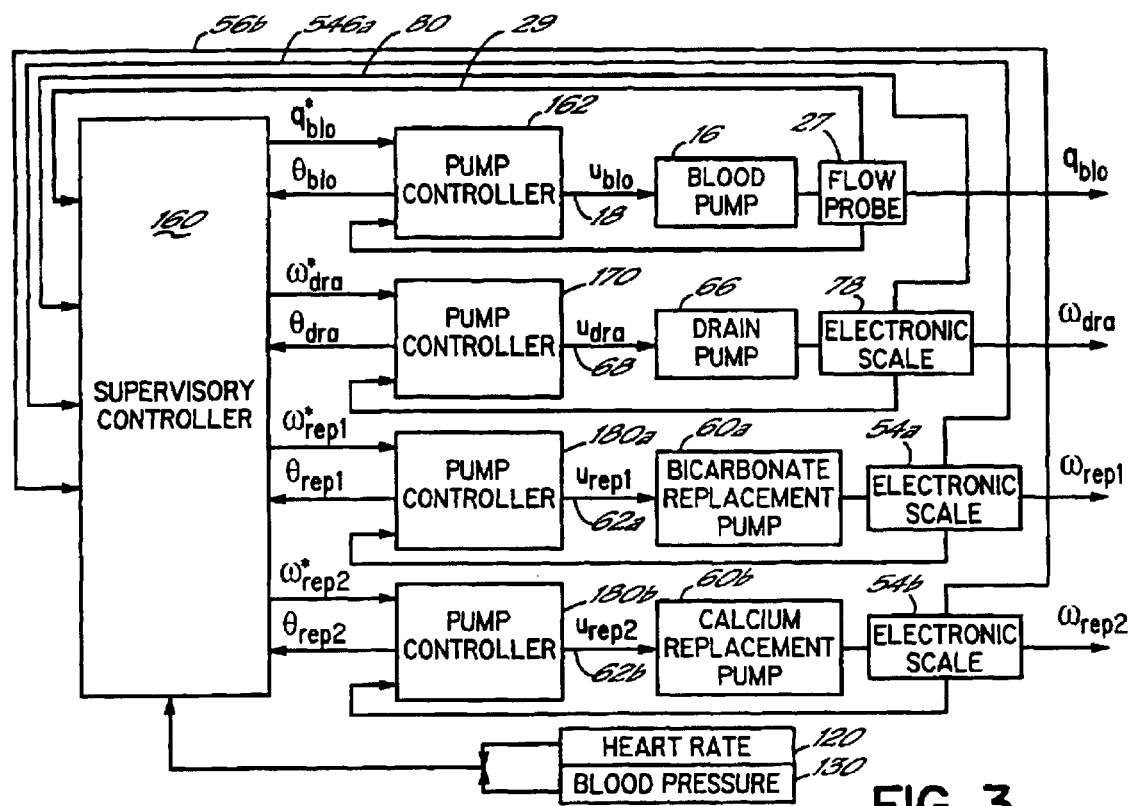
FIG. 3 diagrammatically illustrates the hierarchical control architecture for a hemofiltration system.

FIG. 3 represents a hierarchal control architecture that may be implemented by the computer controller 12 of FIG. 2 for controlling the pumping rates in the hemofiltration system 10 to perform an ultrafiltration or hemodialysis procedure, referred to hereinafter collectively as an ultrafiltration procedure. Because of the commonality of many of the system components in FIG. 3, vis-a-vis the system depicted in FIGS. 1 and 2, like reference numerals are intended to indicate like components. Furthermore, the system components in FIG. 3 operate in the same manner as the corresponding system components shown in FIGS. 1 and 2 and described hereinabove. The hierarchal control architecture disclosed herein is further described in "Intelligent Control of Continuous Venovenous Hemofiltration," Efrain O. Morales, Master's Thesis, University of Cincinnati, Department of Electrical & Computer Engineering and Computer Science, and in "Hierarchical Adaptive and Supervisory Control of Continuous Venovenous Hemofiltration," Efrain O. Morales, Marios M. Polycarpou, Nat Hemasilpin, and John. J. Bissler, submitted to IEEE Transactions on Control Systems Technology, to be published, both of which are hereby incorporated by reference in their entirety.

Referring to FIG. 3, the supervisory controller 160 controls a blood pump 16, a drain pump 66, and a pair of infusate pumps 60, namely a bicarbonate replacement pump 60a and a calcium replacement pump 60b. Pumps 60a, 60b provide replacement fluids to replace fluid volume removed from the patient during the ultrafiltration procedure. The actual weight $\omega_{rep1}(n)$, $\omega_{rep2}(n)$ of each replacement fluid supplied to the patient is respectively monitored by an electronic scale 54a, 54b (where each scale is similar to scale 54 shown in FIG. 2) with a frequency of a sample period n. In a typical ultrafiltration procedure, the sample period is on the order of one second. The actual weight $\omega_{dra}(n)$ of the drained fluid is monitored by an electronic scale 78. The ultrafiltration rate is calculated as the difference between the rate change in drained fluid weight and the rate change in the replacement fluid weight. The actual flow $q_{blo}(n)$ from blood pump 16 is indicated by a flow probe 27.

Blood pump 16 is controlled by an adaptive pump controller 162, implemented in the controller 12, which receives a desired fluid flow rate $q_{blo}^*(n)$ calculated by the supervisory controller 160 as a reference command input. The pump controller 162 is operably connected to the blood pump 16 via line 18 for transmitting a voltage $u_{blo}(n)$ which corresponds to the desired pumping rate and which is proportional to $q_{blo}^*(n)$. The actual flow $q_{blo}(n)$ measure by the flow probe 27 is provided as a feedback signal via line 29 to the supervisory controller 160 and to the pump controller 162. The pump controller 162 further provides a controller parameter vector $\theta_{blo}$, indicative of the tracking performance, to the supervisory controller 160.

Drain pump 66 is controlled by an adaptive pump controller 170, implemented in the controller 12, which receives a desired weight signal $\omega_{dra}^*(n)$ calculated by the supervisory controller 160 as a reference command input. The pump controller 170 is operably connected to the drain pump 66 via line 68 for transmitting a voltage $u_{dra}(n)$ which corresponds to the desired pumping rate and is proportional to the rate change of $\omega_{dra}^*(n)$. The actual weight $\omega_{dra}(n)$ measured by the scale 78 is provided as a feedback signal via line 80 to the supervisory controller 160 and to the pump controller 170. The pump controller 170 further provides a controller parameter vector $\theta_{dra}$, indicative of the tracking performance, to the supervisory controller 160.

Bicarbonate replacement pump 60a and calcium replacement pump 60b are controlled by a respective adaptive pump controller 180a, 180b, both implemented in the controller 12, which receives a desired weight signal $\omega_{rep1}^*(n)$, $\omega_{rep2}^*(n)$ calculated by the supervisory controller 160 as a reference command input. The pump controller 162 is operably connected via a respective line 62a, 62b (similar to line 62 shown in FIG. 2) to the respective pump 60a, 60b for transmitting a respective voltage $u_{rep1}(n)$, $u_{rep2}(n)$ which corresponds to the desired pumping rate and is proportional to the rate change of $\omega_{rep1}^*(n)$, $\omega_{rep2}^*(n)$, respectively. The actual weight $\omega_{rep1}(n)$, $\omega_{rep2}(n)$ measured by the respective scale 54a, 54b is provided as a feedback signal via line 56a, 56b, respectively, to the supervisory controller 160 and to the respective pump controller 180a, 180b. Each pump controller 180a, 180b further provides a respective controller parameter vector $\theta_{rep1}$, $\theta_{rep2}$ indicative of the tracking performance between desired and actual flow rates, to the supervisory controller 160.

The supervisory controller 160 uses a parameter projection feature to remove an input saturation nonlinearity, such that the pumps 16, 60a, 60b, 66 can each be viewed as a linear system. The adaptation of the controller parameters enables enhanced tracking of the pump controllers 162, 170, 180a, 180b in the presence of time variations in flow due to, for example, changes in tubing diameters and wear, changes in hemofilter characteristics, or changes in flow resistance in the blood line.

If the respective applied voltage $u_{dra}(n)$, $u_{rep1}(n)$, $u_{rep2}(n)$ is limited to the linear regime of pump operation, the replacement pumps 60a, 60b and the drain pump 66 are each adequately modeled by a time-varying auto-regressive moving average (ARMA) adaptive control algorithm. The adaptive control algorithm can be expressed as:

$$\omega(n)-b_1^*(n-1)\omega(n-1)+b_2^*(n-1)\omega(n-2)=a_0^*(n-1)+a_1^*(n-1)u(n-1)$$

that relates the actual weights $\omega_{dra}(n)$, $\omega_{rep1}(n)$, $\omega_{rep2}(n)$ and the corresponding applied voltages $u_{dra}(n)$, $u_{rep1}(n)$, $u_{rep2}(n)$. A unique set of respective system parameters $a_0^*$, $a_1^*$, $b_1^*$, $b_2^*$ is ascribed to each pump 60a, 60b, 66. The system parameters $a_0^*$, $a_1^*$, $b_1^*$, $b_2^*$ are unknown time-varying parameters assumed to vary slowly in the absence of disturbances and $a_1^*$ is assumed to be positive since the pump motor never turns the rollers in a reverse direction. The bias parameter $a_0^*$ is included in the equation because it is possible for a pump to induce no fluid flow for a non-zero voltage.

Employing a direct adaptive control scheme, designed to track the desired weight signal $\omega^*(n)$, the control voltage is determined from:

$$u(n-1)=\theta^T(n-1)\phi(n-1)$$
$$\theta^T(n-1):=[\theta_1(n-1)\theta_2(n-1)\theta_3(n-1)\theta_4(n-1)]$$
$$\phi^T(n-1):=[1-\omega(n-1)-\omega(n-2)\omega^*(n)],$$

where $\theta(n)$ is a vector whose components are the controller parameters generated by an adaptive law and $\phi(n)$ is a regressor vector, where $|\phi(n)| \geq 1$ for all $n \geq 0$. If $e(n):=\omega(n)-\omega^*(n)$ denotes the tracking error for the accumulated fluid weight, then the tracking error satisfies:

$$e(n)=a_1^*(\theta(n-1)-\theta^*)^T\phi(n-1),$$

where $\theta^*$ represents the unknown "optimal" parameter vector $$\theta^* = \frac{1}{a_1^*}[-a_0^* - b_1^* - b_2^* I]^T$$

Although the dependence of $\theta^*$ on sample time n is not explicit, $\theta^*$ will vary slowly with time, which is one of the main motivations for the utilization of on-line parameter estimation and adaptive control techniques. In general, the derivation of provably stable adaptive control algorithms for linear time-varying systems is complex. Due to the slowly time-varying nature of the pump dynamics, standard adaptive control methods with $\theta^*$ constant were found to be satisfactory for the present invention.

Pumps in an ultrafiltration system typically exhibit saturation behavior at the lower and upper end of the operation. Specifically, below a certain voltage level the rollers of the pump cease to rotate and fluid flow ceases. Similarly, there is a maximum allowable control voltage, typically specified by the pump manufacturer. Due to saturation in the control signal for pumps, the standard adaptive control must be modified such that the inequality $u_l \leq \theta^T(n)\phi(n) \leq u_h$ holds, where the positive constants $u_l$ and $u_h$ are, respectively, the minimum and maximum allowable control voltages. To address the time-varying parametric uncertainty and input saturations, the following normalized gradient adaptive law with planar projections apply:

$$\theta(n) = \theta(n-1) - \frac{\gamma 0^e(n)}{|\phi(n-1)|^2}\phi(n-1) - p(n)$$

$$p(n): = I(\mu^T(n)\phi(n-1), u_l)\left[\frac{\mu^T(n)\phi(n-1) - u_l}{|\phi(n-1)|^2}\right]\phi(n-1) +$$

$$I(u_h, \mu^T(n)\phi(n-1))\left[\frac{\mu^T(n)\phi(n-1) - u_h}{|\phi(n-1)|^2}\right]\phi(n-1)$$

$$\mu(n): = \theta(n-1) - \frac{\gamma 0^e(n)}{|\phi(n-1)|^2}\phi(n-1)$$

where adaptive step-size $\gamma_0$ is chosen such that it satisfies $0<\gamma_0<2[\sup_n a_1^*(n)]^{-1}$, where an upper bound of $a_1^*$ is assumed to be known. The indicator function $I(*,*)$ is defined as:

$$I(x_1, x_2): = \begin{cases} 1 & \text{if } x_1 < x_2 \\ 0 & \text{otherwise} \end{cases}$$

The projection term $p(n)$ guarantees that the controller parameters $\theta(n)$ will be projected onto the hyperplane $\theta^T\phi(n-1)-u_l=0$ if $\mu^T(n)\phi(n-1)<u_l$. Similarly, the controller parameters $\theta(n)$ will be projected onto the hyperplane $\theta^T\phi(n-1)-u_h=0$ if $\mu^T(n)\phi(n-1)>u_h$. Thus the parameter estimates $\theta(n)$ are adapted such that the control voltage is restricted to a value between $u_l$ and $u_h$.

If the applied voltage $u_{blo}(n)$ is limited to the linear regime of pump operation, the blood pump 16 is adequately modeled by on ARMA adaptive control algorithm, that may be expressed as:

$$q_{blo}(n)+b_1^{blo}(n-1)q_{blo}(n-1)=a_0^{blo}(n-1)+a_1^{blo}(n-1)u_{blo}(n-1).$$

that relates the actual flow $q_{blo}(n)$ and the applied voltage $u_{blo}(n)$ at the $n^{th}$ sample time. The system parameters $a_0^{blo}$, $a_1^{blo}$, $b_1^{blo}$ are assumed to vary slowly over time in the absence of disturbances and $a_1^{blo}$ is assumed to be positive.

A minimum applied voltage is chosen as a value slightly above the voltage for which the rollers of the blood pump 16 can overcome friction and rotate. If the applied voltage never falls below the minimum voltage, the blood flow is never static during the ultrafiltration procedure and the possibility of clotting is reduced. The minimum voltage will depend upon the properties of the tubing used. A typical minimum voltage is 0.3 volts. A maximum voltage will be provided by the pump manufacturer. A typical maximum voltage is 3.2 volts.

The control law is expressed by $u_{blo}(n)=\theta_{blo}^T(n)\phi_{blo}(n)$, where $\theta_{blo}(n)$ is a vector consisting of the three controller parameters, as known for a direct adaptive control scheme, and $\phi_{blo}(n)$ is given by:

$$\phi_{blo}^T(n-1)=[1-q_{blo}(n-1)q_{blo}^*(n)].$$

The desired fluid flow $q_{blo}^*(n)$ is the output of a low-pass filter $$L_{blo}(z) = 0.2514\frac{z+0.99}{z-0.5}$$

which provides a smooth response to required changes in the desired flow rate. For example, the blood pump 16 start-up will be smooth so that the catheter will not draw against the vessel wall.

Figure 4:
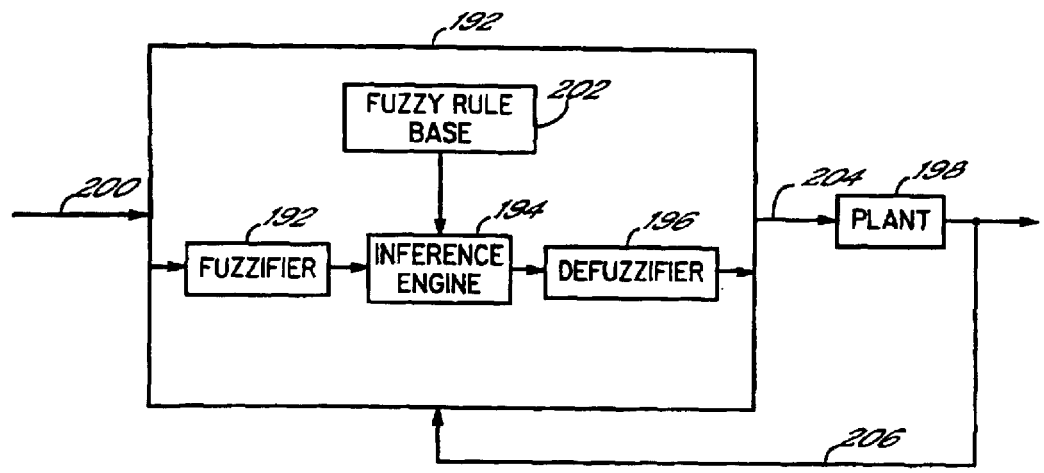
FIG. 4 diagrammatically illustrates the fuzzy logic process performed by the supervisory controller of FIG. 3.

FIG. 4 generically illustrates the fuzzy logic process that may be implemented in a microprocessor, such as by supervisory controller 160 implemented in computer controller 12, for decision-making to control a process, such as an ultrafiltration procedure. As is familiar from fuzzy logic theory, a fuzzy logic control system 190 generally comprises a fuzzifier 192, an inference engine 194, and a defuzzifier 196 for controlling a plant 198. The fuzzifier 192 accepts one or more discrete input data signals 200 and forms a fuzzy set by assigning degrees of membership in a set of input membership functions. The inference engine 194 makes one or more fuzzy inferences from the input signals 200 based on a fuzzy rule base 202. The defuzzifier 196 defuzzifies the fuzzy inferences based upon a set of output membership functions and provides a discrete output control signal 204 to the plant 198. The fuzzy rule base 202 comprises expert knowledge regarding the operational protocol of the system being controlled and comprises sets of "if-then" rules for controlling the plant 198. The defuzzifier 196 may apply various mathematical techniques known in the art of fuzzy logic to defuzzify the fuzzy inferences. The plant 198 may supply feedback signals 206, relating to performance of the plant 198, to the fuzzy logic control system 190 for use by the inference engine 194.

Fuzzification and defuzzification compose the interface needed between measured physical quantities (inputs 200 and outputs 204) and the fuzzy inference engine 194. The resulting mathematical relation is a fuzzy system. The fuzzy system accepts as inputs crisp values, forms fuzzy sets from these values, makes an inference from the specified rule base 202, and provides a crisp output by defuzzifying the inferred fuzzy output.

In the present invention, the plant 168 is the hemofiltration system 10, the fuzzy logic control system 190 is implemented by software in the computer controller 12 for controlling the pumps 16, 60a, 60b, 66, and the input data signals 200 are the patient heart rate 120 and the patient blood pressure 130. The patient heart rate 120 is typically measured in beats per minute (bpm) and the patient blood pressure 130 is typically measured in millimeters of mercury (mmHg). Relying upon the expert clinical knowledge of a physician, an exemplary fuzzy rule base 202 for modifying the ultrafiltration rate based upon the heart rate 120 ($R_h$) and the blood pressure 130 ($P_b$) has the following set of Supervisory Rules:

Supervisory Rule (1): If $R_h$ is high and $P_b$ is normal or low, then decrease ultrafiltration. Wait 10 minutes.

Supervisory Rule (2): If $P_b$ is low and $R_h$ is normal or high, then decrease ultrafiltration. Wait 10 minutes.

Supervisory Rule (3): If both $P_b$ and $R_h$ are low then provide the user with a choice between a decrease or increase of the ultrafiltration rate. Wait 5 minutes.

Supervisory Rule (4): If both $P_b$ and $R_h$ are high for 30 consecutive minutes, then provide the user with a choice between a decrease or increase of the ultrafiltration rate.

Supervisory Rule (5): If $P_b$ is high and $R_h$ is low for 60 consecutive minutes, then increase ultrafiltration.

Supervisory Rule (6): The lowest possible value of ultrafiltration is 0 ml./hr. The highest possible value of the ultrafiltration rate is 30% above that of the ultrafiltration rate specified by the physician, and can thus be changed during the ultrafiltration procedure if so desired.

Supervisory Rule (7): If an increase in ultrafiltration occurs such that the filtered fraction (proportional to the ratio of the desired drained rate to the desired blood flow rate) is greater than 20%, increase the blood pump flow such that the filtered fraction equals 0.2.

Supervisory Rules 1–5 were implemented using fuzzy logic techniques while Supervisory Rules 6 and 7 were incorporated into the supervisory algorithm based on standard switching (crisp) logic methods. The instructions to wait in Supervisory Rules 1–5 are local to each rule. For example, if the ultrafiltration is decreased because Supervisory Rule 1 is satisfied, Supervisory Rule 1 cannot operate again until 10 minutes have lapsed. However, the ultrafiltration rate may be modified if one of Supervisory Rules 2–7 is subsequently triggered. Other sets of Supervisory Rules would be apparent to one of ordinary skill in the art and the Supervisory Rules may be so varied without departing from the scope and spirit of the present invention. For example, a time-independent set of Supervisory Rules is formulated below.

High and low thresholds of heart rate ($R_{high}$, $R_{low}$) and blood pressure ($P_{high}$, $P_{low}$) are specified to the supervisory controller 160 based on the size and cardiovascular state of the patient These thresholds are used by the supervisory controller 160 to characterize the magnitudes of the heart rate 120 and the blood pressure 130 according to the following inequalities. If $R_{low} < R_h < R_{high}$, then the heart rate 120 is deemed normal. If $R_{low} > R_h$, then the heart rate 120 is characterized as being low, and if $R_h > R_{high}$ then the heart rate 120 is high. Similar inequalities apply to characterize the blood pressure 130. The thresholds may be changed during the ultrafiltration procedure to respond to changes in the patient's cardiovascular state.

Figure 5:
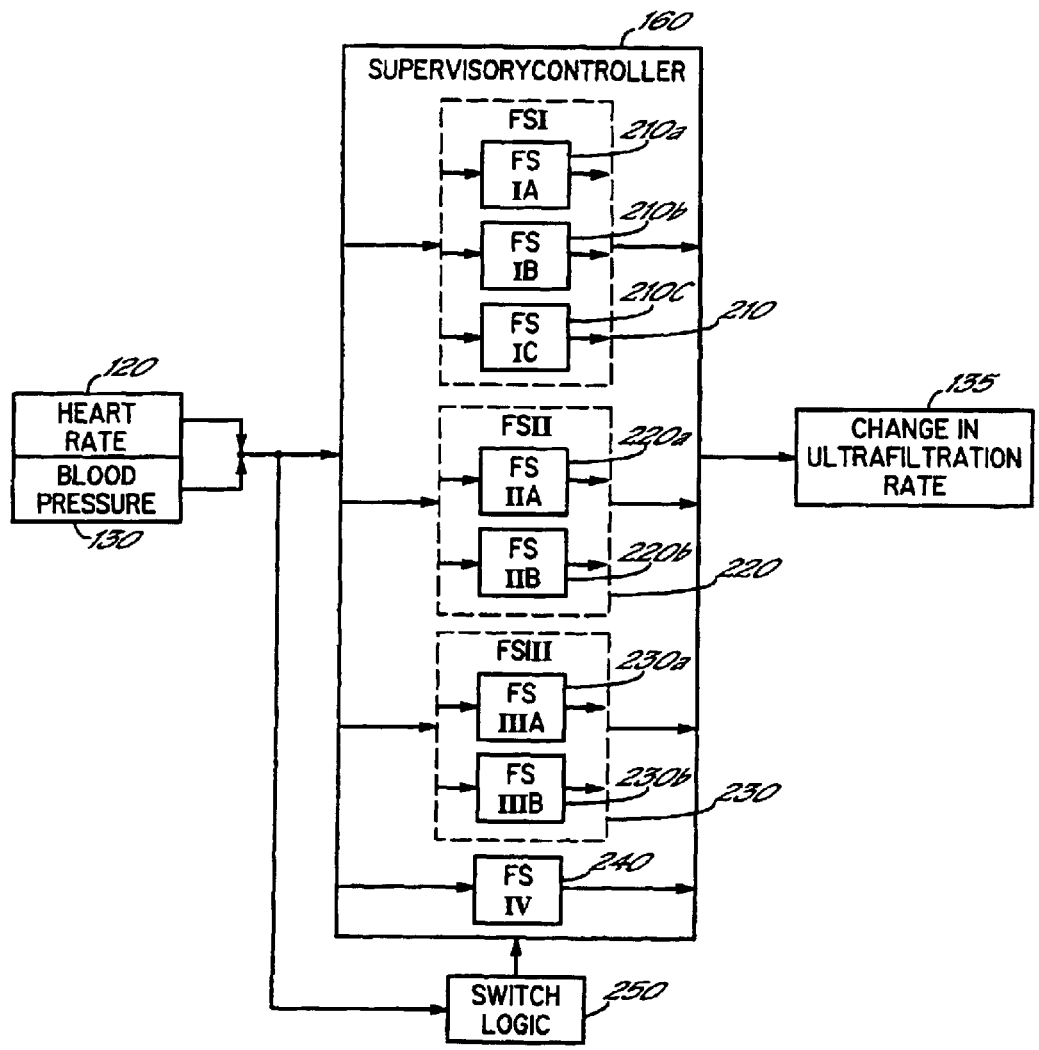
FIG. 5 represents the supervisory control architecture implemented in the supervisory controller.

FIG. 5 diagrammatically illustrates the supervisory controller 160 according to the principles of the present invention in which time has been eliminated as an input parameter. The supervisory controller 160 comprises four separate fuzzy systems 210, 220, 230, 240 that a switch logic 250 activates based upon whether the heart rate 120 and blood pressure 130 are low, normal or high. Only one of the fuzzy systems 210, 220, 230, 240 may be active at a given time. The switch logic 250 also performs the operation of waiting the required duration before or after a supervisory adjustment to the ultrafiltration as required by the Supervisor Rules.

Figure 6A:
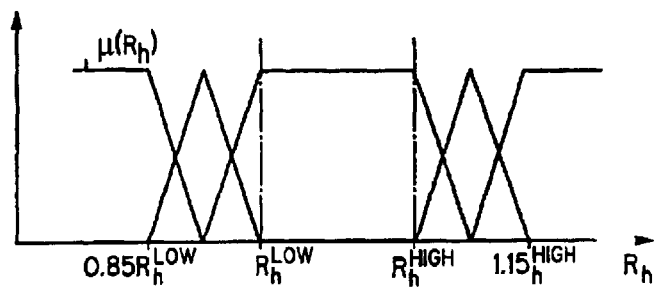
FIG. 6A is a set of membership functions for blood pressure data signals that are input into the fuzzy logic control system.
Figure 6B:
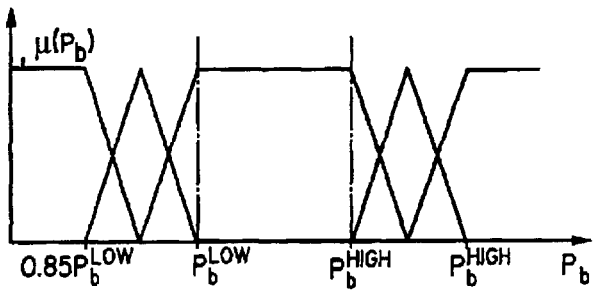
FIG. 6B is a set of input membership functions for heart rate data signals that are input into the fuzzy logic control system.
Figure 6C:
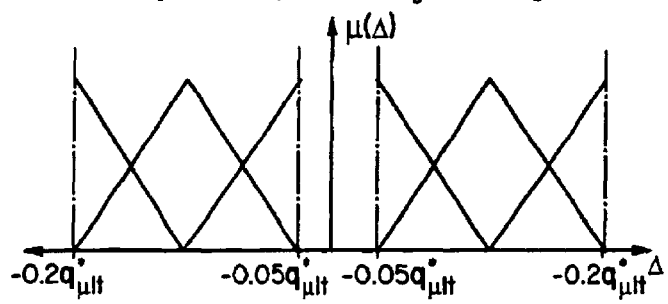
FIG. 6C is a set of output membership functions for signals representing changes in ultrafiltration rate that are output from the fuzzy logic control system.

FIGS. 6A and 6B are two sets of input membership functions defined for the input data signals of heart rate 120 and blood pressure 130, respectively, provided to the supervisory controller 160. FIG. 6C is a set of output membership functions defined for the output data signal connoting the change 135 in ultrafiltration rate for use in defuzzifying the fuzzy inferences made by fuzzy systems 210, 220, 230, 240. Points on each membership function represent the degree of confidence, ranging between 0 and 1, that any single input data signal 120, 130 or output control signal 135 belongs to a particular fuzzy region. Due to overlaps, one input data signal 120, 130 or output data signal 135 may belong to more than one membership function. The membership functions may be varied to have differing gradations as understood by one of ordinary skill in the art of fuzzy logic.

Each individual input membership function and output membership function is defined as a distinct curve having a center and a full-width. In the example of this description, individual membership functions are chosen from curves having characteristic shapes such as a triangular (T) function, a right trapezoidal (RT) function, a left trapezoidal (LT) function, or a constant value (C) function. Alternative characteristic shapes could be selected depending upon the desired response without departing from the spirit and scope of the present invention.

With reference to FIGS. 6A–C, Table 1 summarizes the input and output membership functions for the following universe of discourse:

$$U_1 = (-\infty, R_h^{low}] \quad U_2 = (R_h^{low}, R_h^{high}) \quad U_3 = [R_h^{high}, +\infty)$$

$$V_1 = (-\infty, P_b^{low}] \quad V_2 = (P_b^{low}, P_b^{high}) \quad V_3 = [P_b^{high}, +\infty)$$

$$Y_1 = (-0.2 q_{ult}^*, -0.05 q_{ult}^*] \quad Y_2 = (+0.05 q_{ult}^*, +0.2 q_{ult}^*]$$

where $q_{ult}^*(n)$ is the desired ultrafiltration rate at the time the supervisory controller 160 is activated.

TABLE 1

| Name | Defined in | Type | Centroid | Width |
|---|---|---|---|---|
| $\mu_{11}^u(R_h)$ | $U_1$ | RT | $0.85 R_h^{low}$ | $0.15 R_h^{low}$ |
| $\mu_{12}^u(R_h)$ | $U_1$ | T | $0.925 R_h^{low}$ | $0.15 R_h^{low}$ |
| $\mu_{13}^u(R_h)$ | $U_1$ | T | $R_h^{low}$ | $0.15 R_h^{low}$ |
| $\mu_2^u(R_h)$ | $U_2$ | C | $\frac{1}{2}(R_h^{high} - R_h^{low})$ | $(R_h^{high} - R_h^{low})$ |
| $\mu_{31}^u(R_h)$ | $U_3$ | T | $R_h^{high}$ | $0.15 R_h^{high}$ |
| $\mu_{32}^u(R_h)$ | $U_3$ | T | $0.925 R_h^{high}$ | $0.15 R_h^{high}$ |
| $\mu_{33}^u(R_h)$ | $U_3$ | LT | $0.85 R_h^{high}$ | $0.15 R_h^{high}$ |
| $\mu_{11}^v(P_b)$ | $V_1$ | RT | $0.85 P_b^{low}$ | $0.15 P_b^{low}$ |
| $\mu_{12}^v(P_b)$ | $V_1$ | T | $0.925 P_b^{low}$ | $0.15 P_b^{low}$ |
| $\mu_{13}^v(P_b)$ | $V_1$ | T | $P_b^{low}$ | $0.15 P_b^{low}$ |
| $\mu_2^v(P_b)$ | $V_2$ | C | $\frac{1}{2}(P_b^{high} - P_b^{low})$ | $P_b^{high} - P_b^{low}$ |
| $\mu_{31}^v(P_b)$ | $V_3$ | T | $P_b^{high}$ | $0.15 P_b^{high}$ |
| $\mu_{32}^v(P_b)$ | $V_3$ | T | $0.925 P_b^{high}$ | $0.15 P_b^{high}$ |
| $\mu_{33}^v(P_b)$ | $V_3$ | LT | $0.85 P_b^{high}$ | $0.15 P_b^{high}$ |
| $\mu_{11}^y(\Delta)$ | $Y_1$ | T | $-0.2 q_{ult}^*$ | $0.15 q_{ult}^*$ |
| $\mu_{12}^y(\Delta)$ | $Y_1$ | T | $-0.125 q_{ult}^*$ | $0.15 q_{ult}^*$ |
| $\mu_{13}^y(\Delta)$ | $Y_1$ | T | $-0.05 q_{ult}^*$ | $0.15 q_{ult}^*$ |
| $\mu_{21}^y(\Delta)$ | $Y_2$ | T | $0.05 q_{ult}^*$ | $0.15 q_{ult}^*$ |
| $\mu_{22}^y(\Delta)$ | $Y_2$ | T | $0.125 q_{ult}^*$ | $0.15 q_{ult}^*$ |
| $\mu_{23}^y(\Delta)$ | $Y_2$ | T | $0.2 q_{ult}^*$ | $0.15 q_{ult}^*$ |

The inputs to the fuzzy systems are the patient heart rate and blood pressure. The output of each fuzzy system 210, 220, 230, 240 is derived by combining the singleton fuzzifier, the fuzzy inferences from each invoked rule, and the center-average defuzzifier. The output of the fuzzy systems, $\Delta(n)$, is a recommended change 135 to the ultrafiltration rate. The change is implemented by keeping the replacement fluid flows constant and adding $\Delta(n)$ to the drain flow rate. That is, once a change in ultrafiltration $\Delta(n)$ is calculated at sample time n, it is applied as follows:

$$q_{rep1}*(n+1)=q_{rep1}*(n)$$

$$q_{rep2}*(n+1)=q_{rep2}*(n)$$

$$q_{dra}*(n+1)=q_{dra}*(n)+\Delta(n)$$

$$q_{ult}*(n+1)=q_{dra}*(n+1)-q_{rep1}*(n+1)-q_{rep2}*(n+1),$$

resulting in an ultrafiltration rate changed by $\Delta(n)$ between sample time n and sample time n+1. The output membership functions may change from sample time to sample time because they are dependent on $q_{ult}*(n)$, and thus the fuzzy system mappings built upon these may also change. This feature was designed such that the ultrafiltration system may be used for any size patient. For example, a neonate requires much smaller changes in flow rates than an adult, a fact reflected by the width of some membership functions being dependent upon the desired ultrafiltration rate.

Fuzzy system 210 (FSI) applies where the heart rate 120 is high and/or the blood pressure 130 is low, as defined in Supervisory Rules 1 and 2, to output a negative number to add to the ultrafiltration rate. Fuzzy system 210 comprises three fuzzy subsystems 210a, 210b, 210c (FSIA, FSIB, FSIC). The switch logic 250 activates fuzzy system 210 if the heart rate 120 is high and the blood pressure 130 is high or low, or if the heart rate 120 is high or low and the blood pressure 130 is low. The switch logic 250 also disables the selection of fuzzy system 210 for 10 minutes and chooses which fuzzy subsystem 210a, 210b, 210c will calculate the decrease in the drain flow rate.

The switch logic 250 activates fuzzy subsystem 210a if $R_h$ is high and $P_b$ is normal. The fuzzy rule base for fuzzy subsystem 210a is:
FSIA Rule (1): If $R_h$ is $\mu_{31}{}^u$ then $\Delta$ is $\mu_{13}{}^y$.
FSIA Rule (2): If $R_h$ is $\mu_{32}{}^u$ then $\Delta$ is $\mu_{12}{}^y$.
FSIA Rule (3): If $R_h$ is $\mu_{33}{}^u$ then $\Delta$ is $\mu_{11}{}^y$.
The switch logic 250 activates fuzzy subsystem 210b if $R_h$ is normal and $P_b$ is high. The fuzzy rule base for fuzzy subsystem 210b is:
FSIB Rule (1): If $P_b$ is $\mu_{11}{}^v$ then $\Delta$ is $\mu_{11}{}^y$.
FSIB Rule (2): If $P_b$ is $\mu_{22}{}^v$ then $\Delta$ is $\mu_{12}{}^y$.
FSIB Rule (3): If $P_b$ is $\mu_{33}{}^v$ then $\Delta$ is $\mu_{13}{}^y$.
The switch logic 250 activates subsystem fuzzy subsystem 210c if $R_h$ is high and $P_b$ is low. The fuzzy rule base for fuzzy subsystem 210c is:
FSIC Rule (1, 1): If $P_b$ is $\mu_{11}{}^v$ and $R_h$ is $\mu_{31}{}^u$ then $\Delta$ is $\mu_{11}{}^y$.
FSIC Rule (1, 2): If $P_b$ is $\mu_{11}{}^v$ and $R_h$ is $\mu_{32}{}^u$ then $\Delta$ is $\mu_{11}{}^y$.
FSIC Rule (1,3): If $P_b$ is $\mu_{11}{}^v$ and $R_h$ is $\mu_{33}{}^u$ then $\Delta$ is $\mu_{11}{}^y$.
FSIC Rule (2,1): If $P_b$ is $\mu_{12}{}^v$ and $R_h$ is $\mu_{31}{}^u$ then $\Delta$ is $\mu_{12}{}^y$.
FSIC Rule (2,2): If $P_b$ is $\mu_{12}{}^v$ and $R_h$ is $\mu_{32}{}^u$ then $\Delta$ is $\mu_{12}{}^y$.
FSIC Rule (2,3): If $P_b$ is $\mu_{12}{}^v$ and $R_h$ is $\mu_{33}{}^u$ then $\Delta$ is $\mu_{11}{}^y$.
FSIC Rule (3,1): If $P_b$ is $\mu_{13}{}^v$ and $R_h$ is $\mu_{31}{}^u$ then $\Delta$ is $\mu_{13}{}^y$.
FSIC Rule (3,2): If $P_b$ is $\mu_{13}{}^v$ and $R_h$ is $\mu_{32}{}^u$ then $\Delta$ is $\mu_{12}{}^y$.
FSIC Rule (3,3): If $P_b$ is $\mu_{13}{}^v$ and $R_h$ is $\mu_{33}{}^u$ then $\Delta$ is $\mu_{11}{}^y$.

The switch logic 250 activates fuzzy system 220 (FSII) if the heart rate 120 and blood pressure 130 are low, as defined in Supervisory Rule 3, to calculate the change 135 in ultrafiltration rate and disables fuzzy system 220 for 10 minutes. Fuzzy system 220 comprises two fuzzy subsystems 220a, 220b (FSIIA, FSIIB). Since the direction of the change 135 in ultrafiltration rate is indeterminate, the switch logic 250 must query the user whether the ultrafiltration rate should be increased or decreased. The user selects fuzzy subsystem 220a to increase the ultrafiltration rate. The fuzzy rule base for fuzzy subsystem 220a is:
Rule (1): If $R_h$ is $\mu_{11}{}^u$ then $\Delta$ is $\mu_{23}{}^y$.
Rule (2): If $R_h$ is $\mu_{12}{}^u$ then $\Delta$ is $\mu_{22}{}^y$.
Rule (3): If $R_h$ is $\mu_{13}{}^u$ then $\Delta$ is $\mu_{21}{}^y$.
Alternatively, the user selects fuzzy subsystem 220b to decrease the ultrafiltration rate. The fuzzy rule base for fuzzy subsystem 220b is:
Rule (1): If $P_b$ is $\mu_{11}{}^v$ then $\Delta$ is $\mu_{11}{}^y$.
Rule (2): If $P_b$ is $\mu_{12}{}^v$ then $\Delta$ is $\mu_{12}{}^y$.
Rule (3): If $P_b$ is $\mu_{13}{}^v$ then $\Delta$ is $\mu_{13}{}^y$.

The switch logic 250 activates f system 230 (FSIII) if the heart rate 120 and blood pressure 130 are both high for 30 consecutive minutes, as defined in Supervisor Rule 4, to calculate the change 135 in ultrafiltration rate. Fuzzy system 230 comprises two fuzzy subsystems 230a, 230b (FSIIIA, FSIIIB). Since the direction of the change 135 in ultrafiltration rate is indeterminate, the user is queried whether the ultrafiltration rate should be increased or decreased. The user manually selects fuzzy subsystem 230a to decrease the ultrafiltration rate. The fuzzy rule base for fuzzy subsystem 230a is:
Rule (1): If $P_b$ is $\mu_{31}{}^v$ then $\Delta$ is $\mu_{21}{}^y$.
Rule (2): If $P_b$ is $\mu_{32}{}^v$ then $\Delta$ is $\mu_{22}{}^y$.
Rule (3): If $P_b$ is $\mu_{33}{}^v$ then $\Delta$ is $\mu_{23}{}^y$.
The user selects fuzzy subsystem 230b to increase the ultrafiltration rate. The fuzzy rule base for fuzzy subsystem 230b is:
Rule (1): If $R_h$ is $\mu_{31}{}^u$ then $\Delta$ is $\mu_{13}{}^y$.
Rule (2): If $R_h$ is $\mu_{32}{}^u$ then $\Delta$ is $\mu_{12}{}^y$.
Rule (3): If $R_h$ is $\mu_{33}{}^u$ then $\Delta$ is $\mu_{11}{}^y$.

Finally, fuzzy system 230 (FS IV) calculates increases in ultrafiltration rate as a consequence of improvement in the patient's condition. The switch logic activates fuzzy system 240 if $R_h$ is low and $P_b$ is high. The fuzzy rule base for fuzzy subsystem 240 is:
Rule (1): If $P_b$ is $\mu_{31}{}^v$ then $\Delta$ is $\mu_{21}{}^y$.
Rule (2): If $P_b$ is $\mu_{32}{}^v$ then $\Delta$ is $\mu_{22}{}^y$.
Rule (3): If $P_b$ is $\mu_{33}{}^v$ then $\Delta$ is $\mu_{23}{}^y$.
The supervisory controller 160 also adjusts the filtered fraction such that the filtered fraction is always less than or equal to 20%, as prescribed by Supervisory Rule 7.

In another aspect, the supervisory control system 160 also validates the measured flow rates by comparing those flow rates with prediction errors based on the pump model. The supervisory control system 180 must ignore inaccurate fluid weight measurements, which are the result of, for example, inadvertent bumps to the electronic scales 54, 78, while accurately detecting significant leaks in the fluid pathways or a disconnected tubing. In the latter instances, the supervisory control system 160 halts the ultrafiltration procedure and triggers audible and visual alarms.

The prediction error for the drain pump 66 and the infusate pump 60 is defined as the difference in the measured accumulated fluid weight and the predicted weight forecast by the pump model. The tracking error is defined as the difference in the predicted fluid weight and the desired fluid weight. For the blood pump 16, fluid flow rates are measured by flow probe 27 and the prediction error and the tracking error are referenced with respect to fluid flow rate.

If, for a given minimum number of consecutive sample periods, the prediction error is greater than a positive constant provided by the pump model and the tracking error is greater than a second positive constant also provided by the pump model, the supervisory controller 160 triggers a supervisory action. If only the prediction error or only the tracking error is large, the parameter estimates by the supervisory controller 160 are not yet tuned to the hemofiltration system 10. If both errors are large and are of the same sign, the pumps 16, 60a, 60b, 66 of the hemofiltration system 10 are halted. If the prediction error and the tracking error are large and of opposite sign, the parameter estimates by the supervisory controller 160 are marginally tuned to the undisturbed hemofiltration system 10, and either an inaccurate measurement or a sudden drastic change in the dynamics of the hemofiltration system 10 has likely occurred. A drastic change in the pump dynamics can only be caused by a significant system fault such as a tubing leak. If an inconsistent weight or flow is sensed for any pump 16, 60a, 60b, 66 for more than a predetermined number of consecutive samples, the supervisory controller 160 disables the hemofiltration system 10 and triggers audible and visual alarms.

Implementation of either or both of the aforementioned adaptive control or supervisory control can increase the autonomy of a hemofiltration system. Various advantages follow from the enhanced autonomy. For example, the continuous monitoring and control reduces medical costs and improves the quality of medical care by reducing the need for intermittent supervision of the ultrafiltration procedure by clinical staff. Further details of the invention will be described in the following examples.

The following examples are simulated ultrafiltration procedures performed with an ultrafiltration system having adaptive control and supervisory control, as described above, wherein either tap water or expired blood functioned as a virtual patient. Since the pump model utilized is based on actual fluid weights or flows and not from pump roller angular speeds, the control performance is independent of the fluid's rheology. While the range of achievable flows may change, the type of fluid used for the simulations is irrelevant from the point of flow tracking.

A sampling period of n=1.75 seconds was used in these examples. This specific sampling period was selected after some initial experimentation, taking into consideration the fact that the instantaneous pump flow is impulsive and only the average flow is of interest. Too small a sampling period may give large variations in flow from sample to sample, resulting in a control signal that varies too rapidly, causing a non-smooth operation. On the other hand, a sampling time of more than a few seconds may result in slow response and large tracking errors.

At the beginning of the simulation in each example, all tubing segments were primed with water, or 150 mEq/L sodium chloride solution if blood is used in the example, to eliminate air bubbles in the lines. A source of measurement noise for the drained weight is the evaporation of drained fluid, which can be prevented by sealing the drain container. Other sources of measurement noise include the swinging of replacement fluid bags due to air drafts, which introduces uncertainty in the weight measurements. Placing the bags and the scales inside an enclosure minimizes this uncertainty and enables the practical use of the scales' accuracy (±0.5 gr) as the sole source of uncertainty in the weight measurements. Flow measurements are taken by an ultrasonic flow-probe (Transonic Systems, Inc.) which is calibrated by the manufacturer for the fluid being used. The accuracy of the flow-probe is ±7% of the measured value, which is a source of blood flow error but not of ultrafiltration error.

The simulation flow rates for the blood, drain, and replacement pumps are chosen to be consistent with those typically used with a neonate as the patient Ultrafiltration is beneficial to smaller patients if small flow rates and a small extracorporeal blood line volume are used. The type and size of tubing and connectors for the blood line are chosen according to the magnitude of the flow rates needed. These components determine the ARMA equation parameters for each pump, which in general will vary in time as the physical characteristics of the components vary over time. Values of adaptive step-size $\gamma_0$, maximum voltage $u_h$, and minimum voltage $u_l$, for purposes of the simulations in the example, are given in Table 2.

TABLE 2

| Pump | $\gamma_0$ | $u_i$ [volts] | $u_h$ [volts] |
|---|---|---|---|
| Drain | 0.1 | 0.6 | 10.0 |
| Replacement 1 | 0.1 | 0.2 | 10.0 |
| Replacement 2 | 0.1 | 0.4 | 5.0 |
| Blood | — | 0.3 | 3.2 |

EXAMPLE 1

Figure 7A:
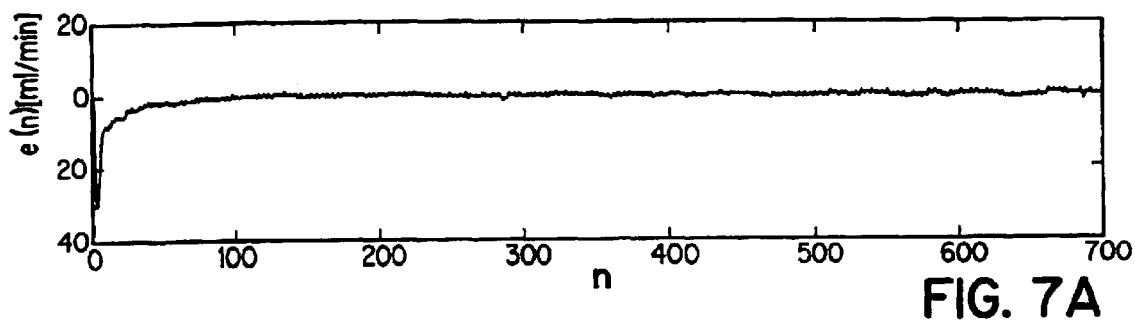
FIG. 7A is a graphical representation of the tracking error of a blood pump for an ultrafiltration simulation.
Figure 7B:
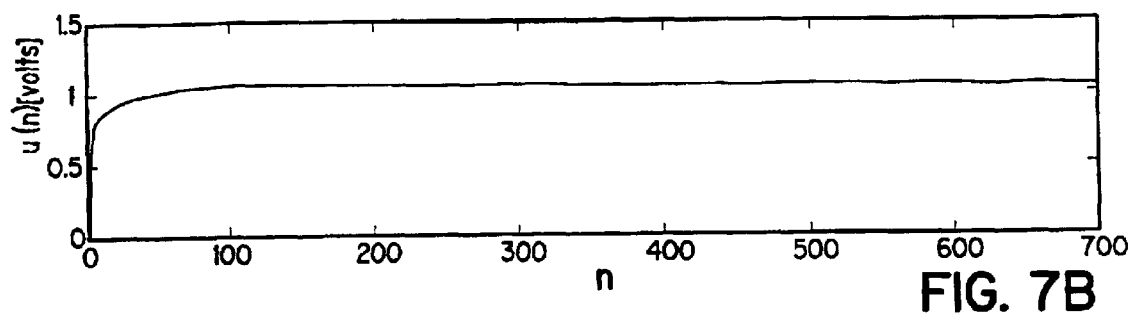
FIG. 7B is a graphical representation of the control voltage for an ultrafiltration simulation.
Figure 7C:
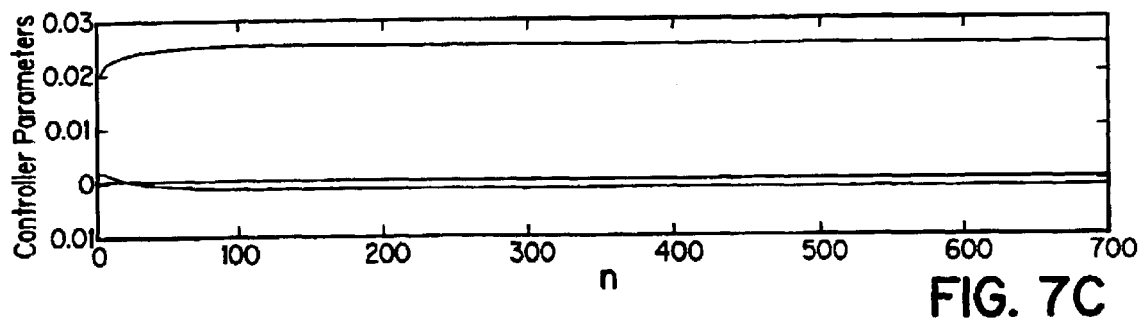
FIG. 7C is a graphical representation of the controller parameters for an ultrafiltration simulation.
Figure 8A:
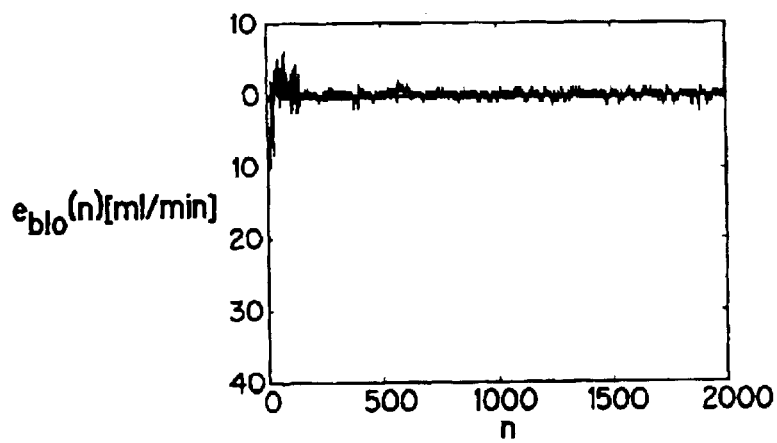
FIG. 8A is a graphical representation of the tracking error of a blood pump for an ultrafiltration simulation.
Figure 8B:
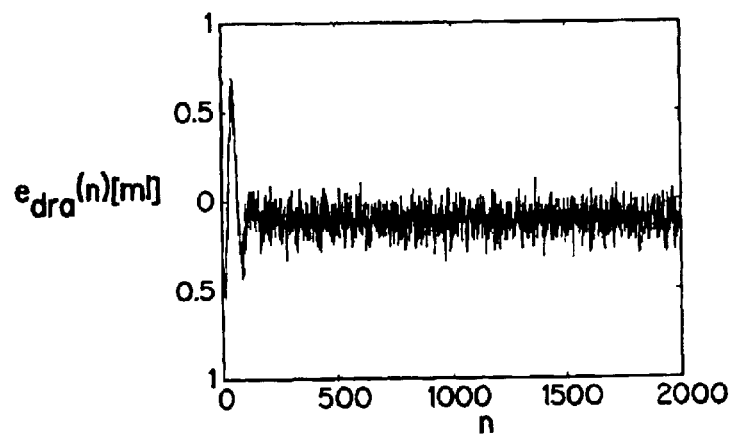
FIG. 8B is a graphical representation of the tracking error of a drain pump for an ultrafiltration simulation.
Figure 8C:
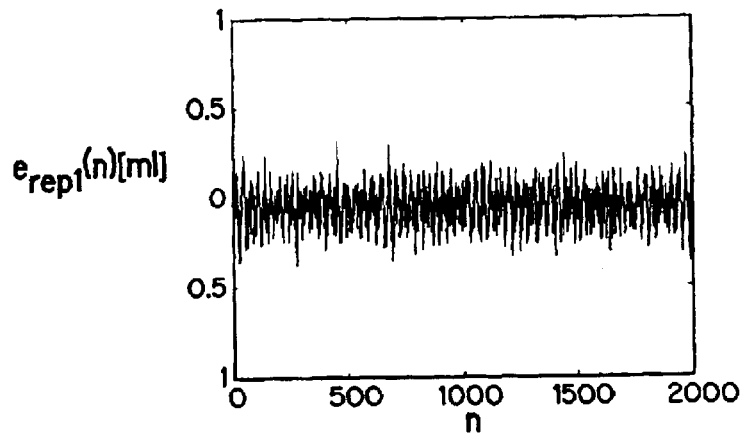
FIG. 8C is a graphical representation of the tracking error of a first replacement pump for an ultrafiltration simulation.
Figure 8D:
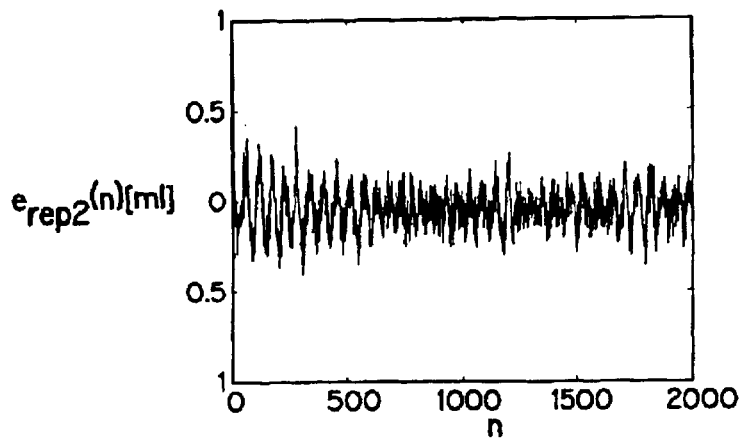
FIG. 8D is a graphical representation of the tracking error of a second replacement pump for an ultrafiltration simulation.

For a ultrafiltration procedure simulated with a container full of blood as the "patient", the tracking error, the control voltage and the controller parameters are shown in FIGS. 7A, 7B, and 7C, respectively. The tracking error goes to zero within thirty seconds, while the voltage remains steady. A large negative blood pump tracking error at the beginning of the ultrafiltration procedure is tolerated because the patient will not be adversely affected by a slow blood clearance of a few seconds. A large positive tracking error could result in decreased tissue perfusion, and the patient may or may not react adversely to the decrease of nutrients reaching various tissues. Hence, a transiently large negative error at the beginning of the ultrafiltration procedure is tolerated in exchange for preventing tracking overshoot.

EXAMPLE 2

A ultrafiltration procedure lasting approximately one hour, with the blood flow rate set at 40.0 ml/min, the drain flow rate set to 230.0 ml/hr, and both replacement flow rates set to 100.0 ml/hr simulates an ultrafiltration procedure performed on a neonate. Typical flow rate and weight tracking errors of a simulation utilizing water as a substitute for all fluids are shown in FIGS. 8A, 8B, 8C and 8D. The blood pump tracking error at the beginning of this simulation differs in character from the beginning of the simulation shown in FIGS. 7A–7C because the flowmeter low pass filter choices provided by the manufacturer were not identical for this time period in the two simulations. Given the precise duration of the procedure, the expected ultrafiltration was 30.1 ml. The ultrafiltration measured by comparing the initial (269.3±0.5 gr) and final weight (241.0±0.5 gr) of the "patient" was 28.3±0.7 gr, which results in a difference of 1.7±0.7 ml from the desired ultrafiltration. The expected ultrafiltration measured by comparing the initial and final weights of drain and replacement fluids was 28.4±1.2 ml. The expected ultrafiltration rate is calculated from the initial weights for the drain and replacement containers 0.0±0.5 gr, 345.2±0.5 gr, and 341.3±0.5 gr, respectively, and the corresponding final weights 230.5±0.5 gr, 243.4±0.5 gr, and 241.0±0.5 gr, respectively, as [(230.5±0.5)–(0.0±0.5)]–[345.2±0.5)–(243.4±0.5)]–[341.3±0.5)–(241.0±0.5)]= 28.4±1.2 gr.

EXAMPLE 3

Figure 9A:
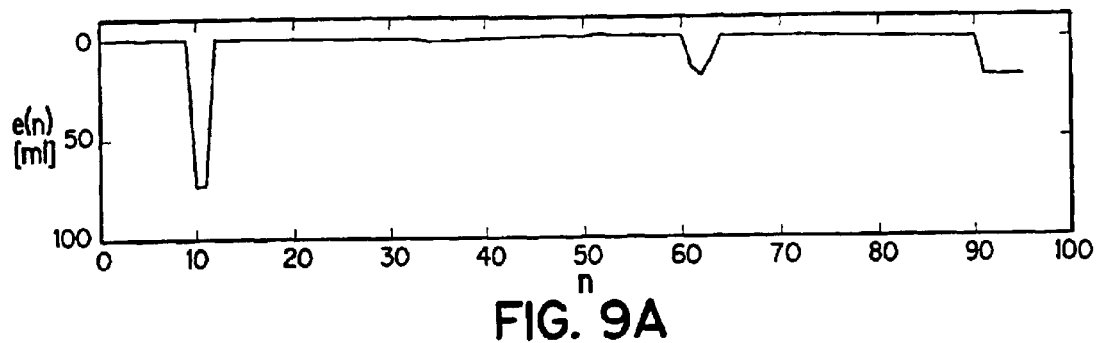
FIG. 9A is a graphical representation of the tracking error of a drain pump for an ultrafiltration simulation.
Figure 9B:
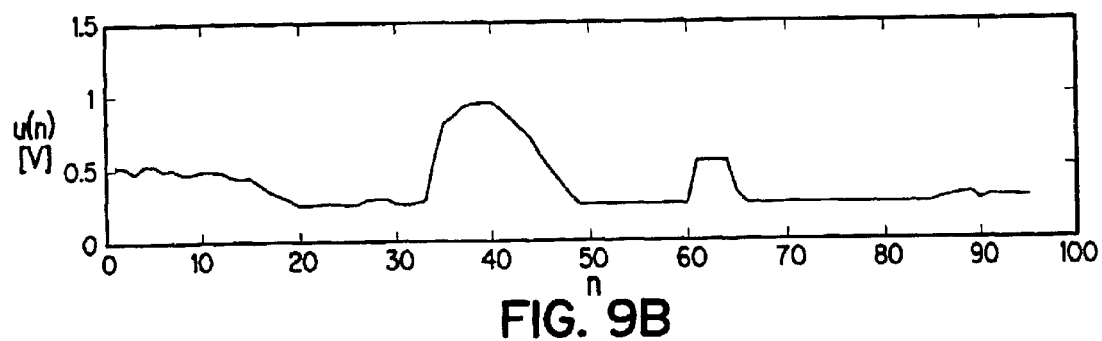
FIG. 9B is a graphical representation of the control voltage for an ultrafiltration simulation.
Figure 9C:
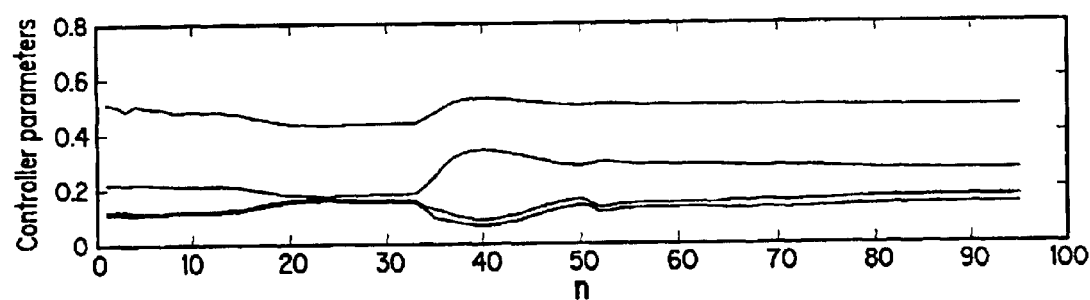
FIG. 9C is a graphical representation of the controller parameters for an ultrafiltration simulation.

FIGS. 9A, 9B, and 9C present a simulation where the scale is bumped twice and a tubing leak occurs. Threshold values for determining an incongruent weight change are given in Table 3.

TABLE 3

| Pump | Maximum Tracking Error | Maximum Prediction Error | Minimum No. of Samples for Validating An Incongruent Measurement of Flow |
|---|---|---|---|
| Blood | 20 ml/min | 20 ml/min | 5 |
| Drain | 3 gr | 3 gr | 5 |
| Replacement 1 | 3 gr | 3 gr | 5 |
| Replacement 2 | 3 gr | 3 gr | 5 |

A brief disturbance of a large magnitude is introduced at a n=10 (by placing a large weight on the scale and removing it), and the supervisory controller does not react. At n=60, a similar, smaller disturbance is introduced for a brief period, and again, the supervisory controller does not respond. At n=90, a similar small disturbance is introduced, but for a prolonged period. This simulates a leak in the tubing, and is a much smaller disturbance than is generally encountered when leaks occur during actual ultrafiltration procedures. The controller detects the incongruent weight change and decides, in this case, to discontinue ultrafiltration.

EXAMPLE 4

Figure 10A:
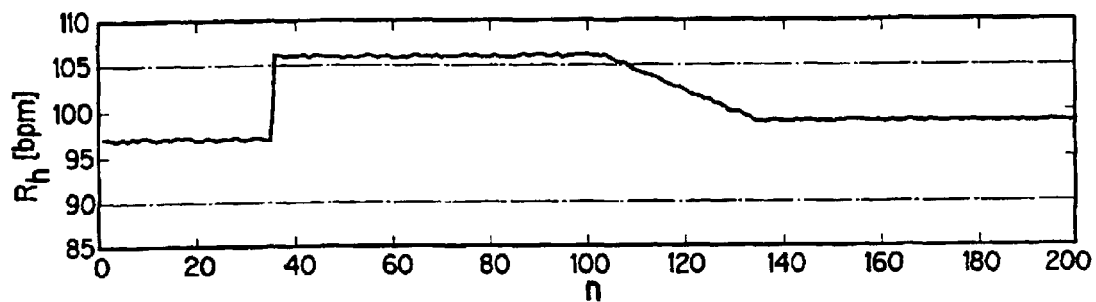
FIG. 10A is a graphical representation of the heart rate for an ultrafiltration simulation.
Figure 10B:
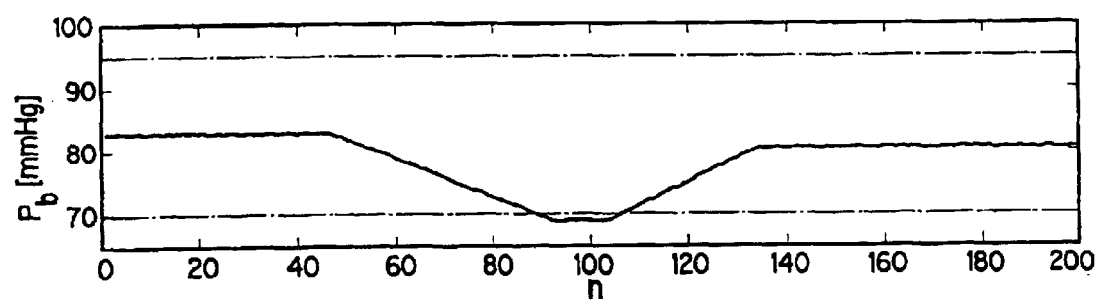
FIG. 10B is a graphical representation of the blood pressure for an ultrafiltration simulation.
Figure 10C:
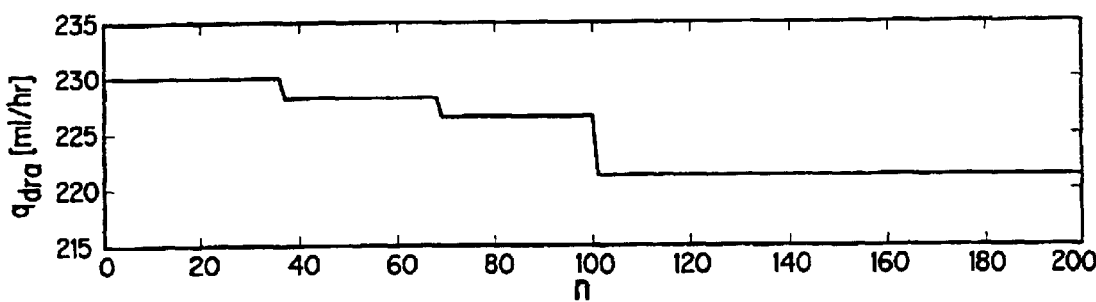
FIG. 10C is a graphical representation of the desired drain flow rate calculated by fuzzy system I for an ultrafiltration simulation.

FIGS. 10A, 10B, and 10C show simulated patient data and the desired drain rate for a simulation of ultrafiltration performed on a neonate The patient heart rate and blood pressure are generated with computer software. The blood flow rate is set to 40 ml/min, and the replacement rates are both set to 100 ml/min. The thresholds for the heart rate are chosen as 90 bpm and 105 bpm, and the thresholds for the blood pressure are chosen as 70 mmHg and 95 mmHg. At the beginning of the simulation, $R_h$ and $P_b$ are within their normal ranges. Around n=40, $R_h$ rises to above the threshold while $P_b$ stays normal. The supervisory controller makes a correction due to the high heart rate and waits for a reaction. During an actual ultrafiltration procedure the supervisory controller would wait about 10 minutes before taking any other actions because of a high heart rate. For purposes of the simulation, the wait is shortened to about 30 seconds. The switch logic once again activates FSIA 30 seconds after the first correction since the patient's heart rate remains high. The supervisory controller waits 30 more seconds, and the switch logic rechecks $R_h$ and $P_b$. This time, the heart rate is high and the blood pressure is low, so the switch logic activates FSIC. The fuzzy subsystem FISC decreases the ultrafiltration rate at about n=100, and shortly thereafter $R_h$ and $P_b$ begin to return to normal. Since the patient parameters return to normal before the supervisory controller checks if the reactivation of FSI is necessary, no further corrections are made.

EXAMPLE 5

Figure 11A:
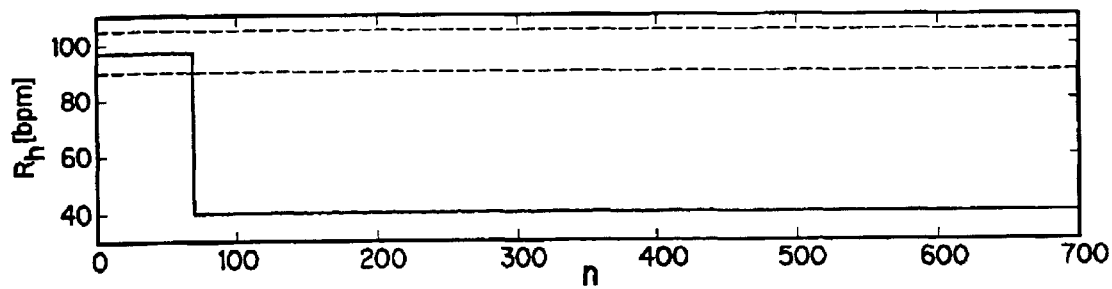
FIG. 11A is a graphical representation of the heart rate for an ultrafiltration simulation.
Figure 11B:
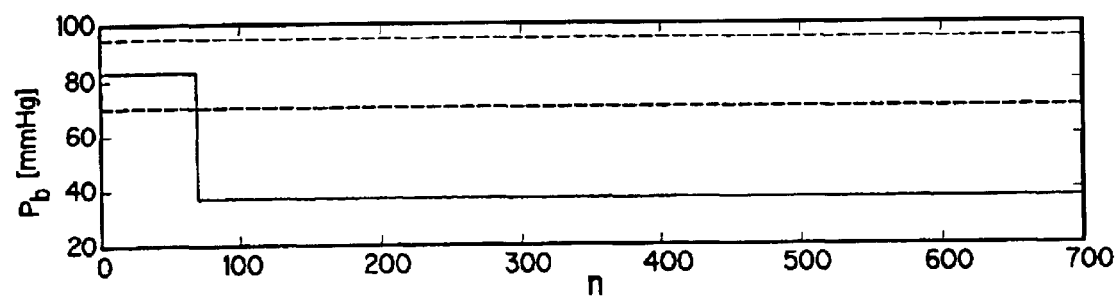
FIG. 11B is a graphical representation of the blood pressure for an ultrafiltration simulation.
Figure 11C:
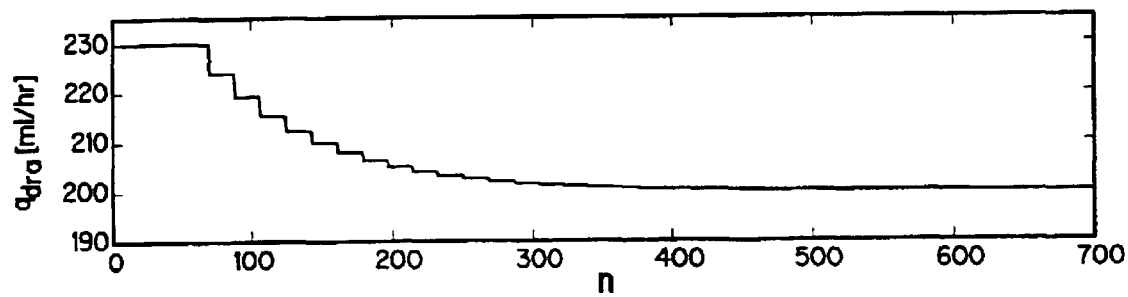
FIG. 11C is a graphical representation of the desired drain flow rate calculated by fuzzy system II for an ultrafiltration simulation.

FIGS. 11A, 11B and 11C show a simulation where the heart rate and blood pressure are both low and the user has specified a decrease of ultrafiltration when queried by the supervisory controller. The blood flow rate is set to 40 ml/min, and the replacement rates are both set to 100 ml/min. The minimum and maximum thresholds for the heart rate are chosen as 90 bpm and 105 bpm, and the minimum and maximum thresholds for the blood pressure are chosen as 70 mmHg and 95 mmHg. At the beginning of the simulation, $R_h$ and $P_b$ are within their normal ranges. At about n=80, $R_h$ and $P_b$ drop below their respective low thresholds, and FSIIB calculates an ultrafiltration rate decrease. The switch logic forces FSII to wait 10 seconds (5 minutes for an actual ultrafiltration procedure) before another adjustment is made. Since the patient parameters never return to their respective normal ranges, the supervisory controller lowers the drain rate until the ultrafiltration rate is zero.

EXAMPLE 6

Figure 12A:
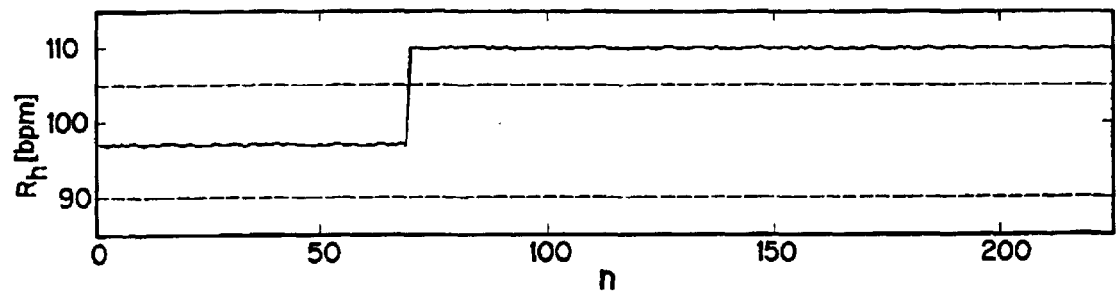
FIG. 12A is a graphical representation of the heart rate for an ultrafiltration simulation.
Figure 12B:
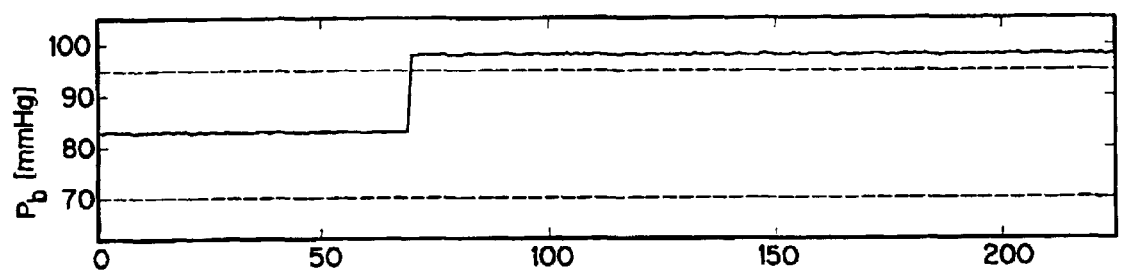
FIG. 12B is a graphical representation of the blood pressure for an ultrafiltration simulation.
Figure 12C:
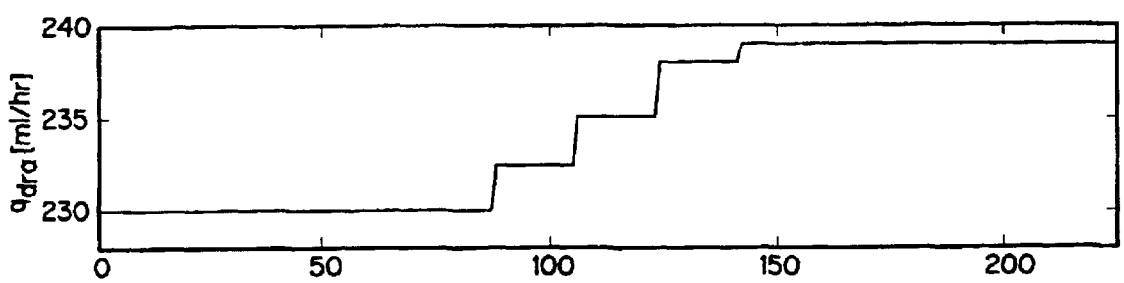
FIG. 12C is a graphical representation of the desired drain flow rate calculated by fuzzy system III for an ultrafiltration simulation.

FIGS. 12A, 12B and 12C show a simulation where the patient parameters are both high and the user specifies an increase of the ultrafiltration rate. The blood flow rate is set to 40 ml/min, and the replacement rates are both set to 100 ml/min. The thresholds for the heart rate are chosen as 90 bpm and 105 bpm, and the thresholds for the blood pressure are chosen as 70 mmHg and 95 mmHg. At the beginning of the simulation, $R_h$ and $P_b$ are within their normal ranges. At about n=60, both the patient heart rate and blood pressure rise above their respective upper thresholds. After 20 seconds (30 minutes in an actual ultrafiltration procedure), the condition for activating FSII is met and the ultrafiltration rate is increased. Since the patient parameters never return to their respective normal ranges, the supervisory controller raises the drain rate until the ultrafiltration rate is 30% above the rate initially given. At this point, the hemofiltrator alerts the user that the maximum ultrafiltration rate has been set as the desired rate.

EXAMPLE 7

Figure 13A:
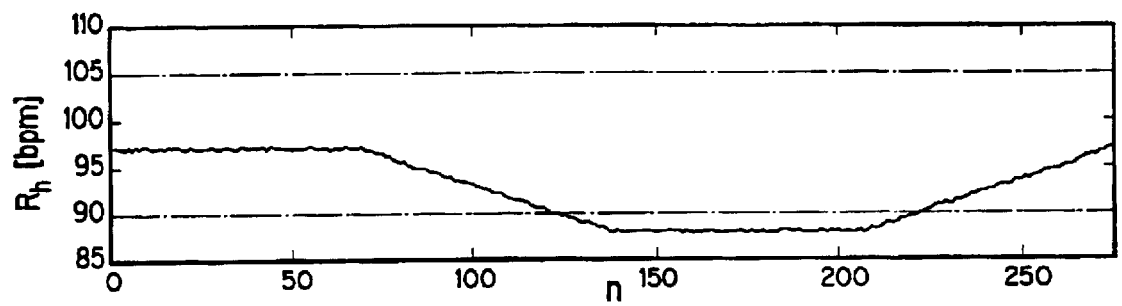
FIG. 13A is a graphical representation of the heart rate for an ultrafiltration simulation.
Figure 13B:
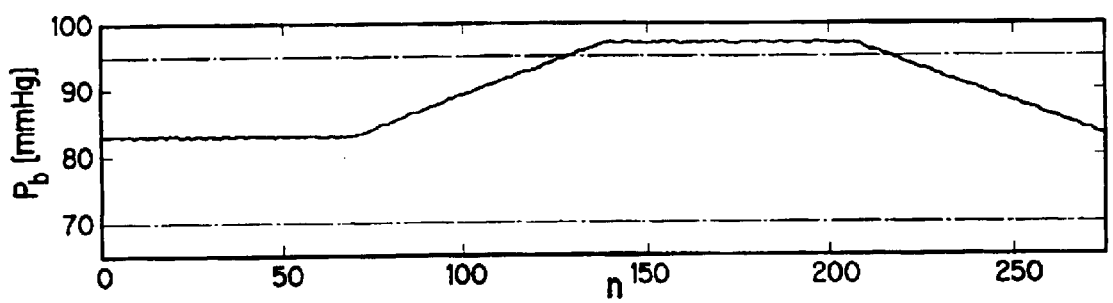
FIG. 13B is a graphical representation of the blood pressure for an ultrafiltration simulation.
Figure 13C:
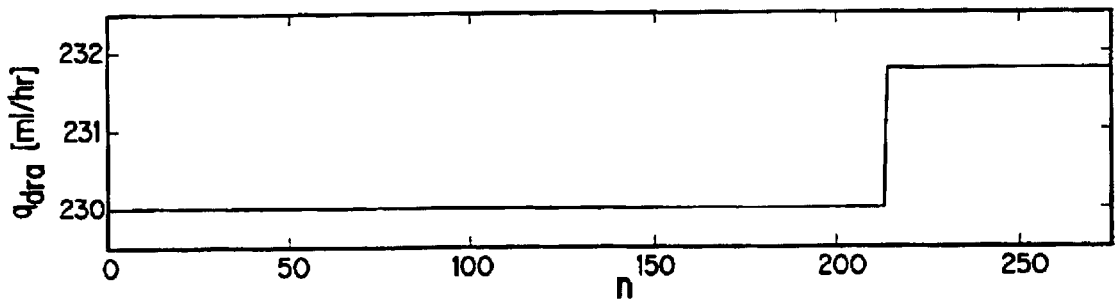
FIG. 13C is a graphical representation of the desired drain flow rate calculated by fuzzy system IV for an ultrafiltration simulation.

FIGS. 13A, 13B and 13C present a simulation where the patient is getting well enough to increase the ultrafiltration rate. The blood flow rate is set to 40 ml/min, and the replacement rates are both set to 100 ml/min. The thresholds for the heart rate are chosen as 90 bpm and 105 bpm, and the thresholds for the blood pressure are chosen as 70 mmHg and 95 mmHg. At the beginning of the simulation, $R_h$ and $P_b$ are within their normal ranges. Once the heart rate and blood pressure are in the favorable regions, the supervisory controller waits 120 seconds (about 60 minutes in an actual ultrafiltration procedure) to detect transient behavior before increasing the drain pump flow rate. Since the heart rate and the blood pressure return to their normal ranges, no further adjustments are made.

EXAMPLE 8

Figure 14A:
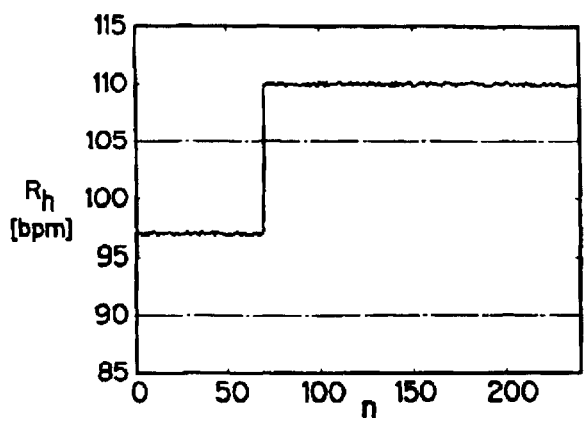
FIG. 14A is a graphical representation of the heart rate for an ultrafiltration simulation.
Figure 14B:
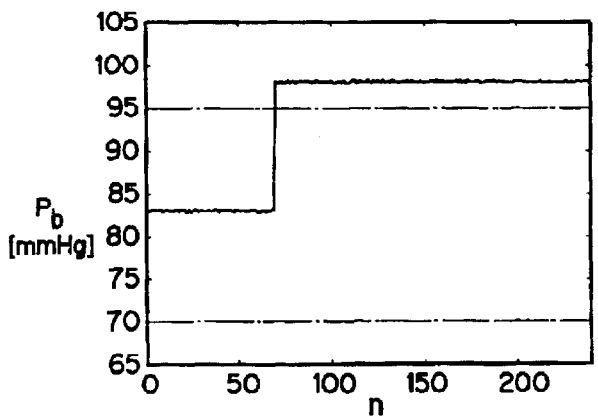
FIG. 14B is a graphical representation of the blood pressure for an ultrafiltration simulation.
Figure 14C:
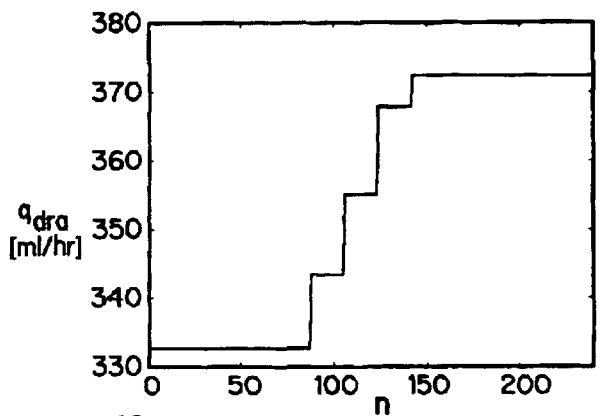
FIG. 14C is a graphical representation of the desired drain flow rate calculated by FSIII for an ultrafiltration simulation
Figure 14D:
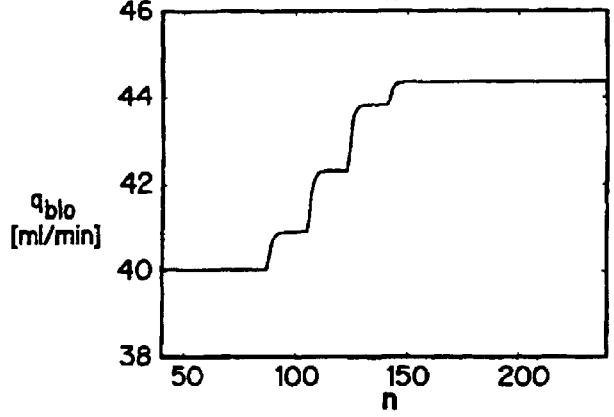
FIG. 14D is a graphical representation of the blood pump flow rate for an ultrafiltration simulation.

FIGS. 14A, 14B and 14C depict a simulation where the supervisory controller adjusts the ultrafiltration due to a high filtered fraction. The patient parameters are both high for an extended period of time and the initial ultrafiltration rate of 132.6 ml/hr is increased to 172.4 ml/hr by increasing the drain rate from 332.6 ml/hr to 372.4 ml/hr. The latter flow rate would give a filtered fraction of 22.2% if the blood pumping were held at 40.0 ml/min. In order to bring the filtered fraction down to 20%, the blood pump flow rate must be increased to 44.3 ml/min.

The supervisory control system and the adaptive control system described above are not limited to use in a ultrafiltration procedure, but may find application in other medical systems that employ a pump for transferring a fluid, such as a heart-lung machine. Other suitable medical applications would be apparent to one of ordinary skill in the art.

It will be appreciated by persons skilled in the art that various modifications can be made to the systems and methods of the present invention.

What is claimed is:

1. A hemofiltration system for fluid removal from the blood of a patient, comprising:

a pump capable of pumping a liquid selected from the group consisting of infusate, drained fluid, and blood in the hemofiltration system;

a sensor for measuring the flow rate of fluid in the medical system generated by at least one pump, the flow rate sensor providing flow rate data signals correlated to the fluid flow rate; and a supervisory controller operably connectable to the at least one pump and operably connected to the flow rate sensor;

at least one monitor for measuring at least one predetermined patient parameter; said least one patient parameter monitor providing patient parameter data signals correlated to said at least one patient parameter, wherein the controller is operably connected to said at least one monitor, the controller receiving the flow rate data signals and the patient parameter data signals and analyzing the flow rate data signals and the patient parameter data signals utilizing fuzzy logic having at least one predetermined supervisory rule, and then providing an output signal for the at least one pump to adjust, as necessary on a periodic ongoing basis, the flow rate of liquid generated by the at least one pump for regulating fluid removal from the patient's blood.

2. The control system of claim 1, wherein said at least one patient parameter monitor is selected from the group consisting of a blood pressure monitor providing blood pressure data signals, a heart rate monitor providing heart rate data signals, and combinations thereof.

3. The control system of claim 2, wherein the medical system is an ultrafiltration system and the at least one predetermined supervisory rule is selected from the group consisting of:

a) If heart rate is high and blood pressure is normal or low, then decrease ultrafiltration and wait a first predetermined time, b) If blood pressure is low and heart rate is normal or high, then decrease ultrafiltration and wait a second predetermined time, c) If blood pressure is low and heart rate is low, then provide the user a choice between a decrease or increase of the ultrafiltration rate and wait a third predetermined time, d) If blood pressure is high and heart rate is high for a fourth predetermined time, then provide the user with a choice between a decrease or increase of the ultrafiltration rate, e) If blood pressure is high and heart rate is low for a fifth predetermined time, then increase ultrafiltration, f) The lowest possible value of ultrafiltration is a predetermined minimum rate per hour and the highest possible value of the ultrafiltration rate is a predetermined percentage above that of a predetermined maximum ultrafiltration rate, g) If an increase in ultrafiltration occurs such that the filtered fraction is greater than a predetermined filtered fraction, then increase the blood pump flow such that the filtered fraction equals the predetermined filtered fraction.

4. The control system of claim 2, wherein the sensor is selected from the group consisting of a flowmeter and a weight scale.

5. The control system of claim 1, further comprising a second sensor for measuring the flow rate of fluid generated by a second pump, the second flow rate sensor providing second flow rate data signals correlated to the fluid flow rate, wherein the supervisory controller is further operably connectable to the second pump and operably connected to the second flow rate sensor, the controller receiving the second flow rate data signals and analyzing the signals utilizing fuzzy logic based on at least one predetermined supervisory rule and the controller then providing an output signal for the second pump to adjust, as necessary on a periodic ongoing basis, the flow rate of fluid generated by the second pump.

6. The control system of claim 5, further comprising a third sensor for measuring the flow rate of fluid in the medical system generated by a third pump, the third flow rate sensor providing third flow rate data signals correlated to the fluid flow rate, wherein the supervisory controller is further operably connectable to the third pump and operably connected to the third flow rate sensor, the controller receiving the third flow rate data signals and analyzing the signals utilizing fuzzy logic based on at least one predetermined supervisory rule and the controller then providing an output signal for the third pump to adjust, as necessary on a periodic ongoing basis, the flow rate of fluid generated by the third pump.

7. The control system of claim 6, further comprising:

a fourth sensor for measuring the flow rate of fluid in the medical system generated by a fourth pump, the fourth flow rate sensor providing fourth flow rate data signals correlated to the fluid flow rate, wherein the supervisory controller is further operably connectable to the fourth pump and operably connected to the fourth flow rate sensor, the controller receiving the fourth flow rate data signals and analyzing the signals utilizing fuzzy logic based on at least one predetermined supervisory rule and the controller then providing an output signal to the fourth pump to adjust, as necessary on a periodic ongoing basis, the flow rate of fluid generated by the fourth pump.

8. The control system of claim 1, further comprising an adaptive controller operably connectable to the pump and to said flow rate sensor, the adaptive controller receiving said flow rate data signals, using an adaptive law to generate a set of controller parameters for correcting time-dependent deviations of the flow rate of the respective fluid from a predetermined blood flow rate, and using a control law to generate an output signal from the set of controller parameters for adjusting the pumping rate of fluid generated by the pump to achieve the predetermined blood flow rate, said adaptive controller then providing the output signal for the pump on a periodic ongoing basis.

9. A hemofiltration system for fluid removal from the blood of a patient, comprising:

a pump capable of pumping a liquid selected from the group consisting of infusate, drained fluid, and blood in the hemofiltration system;

a flow rate sensor for measuring the flow rate of the liquid generated by the at least one pump, the flow rate sensor providing flow rate data signals correlated to the liquid flow rate; and an adaptive controller operably connectable to the at least one pump and operably connected to the flow rate sensor, the controller receiving the flow rate data signals and generating an output signal for adjusting the pumping rate of the liquid generated by the at least one pump, the controller providing the output signal for the at least one pump on a periodic ongoing basis, the controller using an adaptive law to generate a set of controller parameters for correcting time-dependent deviations of the flow rate from a predetermined flow rate, and using a control law to generate the output signal from the set of controller parameters for adjusting the pumping rate of the liquid generated by the at least one pump to achieve the predetermined flow rate for regulating fluid removal from the patient's blood.

10. The control system of claims 9, wherein the adaptive law further includes parameter projections to limit the output signal to a range between a predetermined minimum output signal and a predetermined maximum output signal.

11. The control system of claim 9, wherein the sensor is selected from the group consisting of a flowmeter and a weight scale.

12. The control system of claim 11, wherein the sensor is a weight scale providing weight data signals and the flow rate data signals comprise the rate change in the weight data signals.

13. A method of controlling a pump in a hemofiltration system, comprising:
measuring the flow rate of a liquid selected from the group consisting of infusate, drained fluid, and blood generated by the pump to obtain flow rate data signals correlated to the fluid flow rate;
measuring at least one patient parameter to obtain patient parameter data signals correlated to said at least one patient parameter;
analyzing the flow rate data signals and the patient parameter data signals utilizing fuzzy logic having at least one predetermined supervisory rule; and
providing an output signal to the pump to adjust, as necessary on a periodic ongoing basis, the flow rate of liquid generated by the pump for regulating fluid removal from the patient's blood.

14. A method of controlling a pump in an ultrafiltration system, comprising:
measuring a flow rate of a liquid selected from the group consisting of infusate, drained fluid, and blood in the hemofiltration system generated by the pump to obtain flow rate data signals correlated to the liquid flow rate;
generating a set of controller parameters from the flow rate signals for correcting time-dependent deviations of the flow rate from the predetermined flow rate;
generating an output signal using a control law from the set of controller parameters, the output signal capable of adjusting the pumping rate of liquid generated by the pump to achieve a predetermine flow rate; and
providing the output signal to the pump on a periodic ongoing basis to correct the deviations of the flow rate from the predetermined flow rate for regulating fluid removal from the patient's blood.

15. Hemofiltration method for removal of fluid from the blood of a patient, comprising:
pumping blood from a patient through a hemofilter and back to the patient;
monitoring the blood outflow from the blood pump and generating blood flow rate data signals;
maintaining a supply of infusate in a first reservoir;
monitoring the weight of infusate in the first reservoir and generating infusate flow rate data signals, pumping the infusate to the hemofilter;
pumping drained fluid from the hemofilter into a second reservoir;
monitoring the weight of drained fluid in the second reservoir and generating drained fluid flow rate data signals;
monitoring at least one predetermined patient parameter, such as patient heart rate and/or blood pressure, and generating parameter data signals correlated thereto; and
controlling the pumping rate of the blood, the drained fluid, and the infusate with a programmed computer, the computer being responsive to the flow rate data signals, the computer;
receiving the flow rate data and parameter data signals;
analyzing the received signals with fuzzy logic having at least one predetermined supervisory rule; and
generating an output signal to each pump based upon the analysis of the received flow rate data and parameter data signals to adjust, as necessary on a periodic ongoing basis, the flow rate of fluid generated by each pump, for regulating fluid removal from the patient's blood.

16. Hemofiltration method for removal of fluid from the blood of a patient, comprising
pumping blood from a patient through a hemofilter and back to the patient;
sensing the performance of the blood pump and generating a first set of controller parameters from a fist adaptive law;
monitoring the blood outflow from the blood pump and generating blood flow rate data signals;
maintaining a supply of infusate in a first reservoir;
monitoring the weight of infusate in the first reservoir and generating infusate flow rate data signals;
pumping the infusate to the hemofilter;
sensing the performance of the infusate pump generating a second set of controller parameters from a second adaptive law;
pumping drained fluid from the hemofilter into a second reservoir;
monitoring the weight of drained fluid in the second reservoir and generating drained fluid flow rate data signals;
sensing the performance of the drained fluid pump and generating a third set of controller parameters from a third adaptive law;
controlling the pumping rate of the blood, the drained fluid, and the infusate with a programmed computer to correspond to a set of predetermined pumping rates, the computer being responsive to the flow rate data signals and the controller parameters,
using a control law to generate an output signal from the flow rate data signals and the controller parameters for correcting time-dependent deviations of the flow rate from the set of predetermined pumping rates; and
providing the output signal to at least one pump on a periodic ongoing basis, for regulating fluid removal from the patient's blood.

17. Continuous hemofiltration system for removal of fluid from the blood of a patient, comprising:
a hemofilter;
a first pump for pumping blood from a patient through said hemofilter and back to the patient;
a flowmeter downstream of said first pump to measure the blood outflow rate from the blood pump, said flowmeter generating blood flow rate data signals correlated to the blood outflow rate;
a first reservoir for maintaining a supply of infusate;
a second pump for pumping the infusate firm said first reservoir to said hemofilter;
a second reservoir for receiving drained fluid from said hemofilter;

a third pump for pumping the drained fluid from said hemofilter to said second reservoir; and an adaptive controller operably connected to said first pump and to said blood flowmeter, said adaptive controller receiving said blood flow rate data signals, using an adaptive law to generate a set of controller parameters for correcting time-dependent deviations of the blood outflow rate from a target blood outflow rate, and using a control law to generate an output signal from the set of controller parameters for adjusting the pumping rate of fluid generated by the first pump to achieve the target blood flow rate, said adaptive controller then providing the output signal to the first pump on a periodic ongoing basis for regulating fluid removal from the patient's blood.

18. The continuous hemofiltration system of claim 17, further comprising:

at least one monitor for measuring at least one predetermined patient parameter, said least one patient parameter monitor providing patient parameter data signals correlated to said at least one patient parameter;

a first scale to measure the weight of infusate in said first reservoir, said first scale generating infusate flow rate data signals correlated to the infusate weight;

a second scale to measure the weight of drained fluid in said second reservoir, said second scale generating drained fluid flow rate data signals correlated to the drained fluid weight; and a supervisory controller operably connected to said pumps, to said flowmeter, to said scales, and to said at least one patient parameter monitor, said controller receiving said flow rate data signals and said patient parameter data signals and analyzing said signals utilizing fuzzy logic having at least one predetermined supervisory rule, said controller then providing an output signal to said pumps to adjust, as necessary on a periodic ongoing basis, the flow re of fluid generated by each at least one pump for regulating fluid removal from the patient's blood.

19. Continuous hemofiltration system for removal of fluid from the blood of a patient, comprising:

a hemofilter;

a first pump for pumping blood from a patient through said hemofilter and back to the patient;

a flowmeter downstream of said first pump to measure the blood outflow rate from the blood pump, said flowmeter generating blood flow rate data signals correlated to the blood outflow rate;

a first reservoir for maintaining a supply of infusate;

a first scale to measure the weight of infusate in said first reservoir, said first scale generating infusate flow rate data signals correlated to the infusate weight;

a second pump for pumping the infusate from said first reservoir to said hemofilter;

a second reservoir for receiving drained fluid from said hemofilter;

a second scale to measure the weight of drained fluid in said second reservoir, said second scale generating drained fluid flow rate data signals correlated to the drained fluid weight;

a third pump for pumping the drained fluid from said hemofilter to said second reservoir;

at least one monitor for measuring at least one patient parameter, said least one patient parameter monitor providing patient parameter data signals correlated to said at least one patient parameter; and a supervisory controller operably connected to said first, second and third pumps, to said flowmeter, to said first and second scales, and to said at least one patient parameter monitor, said controller receiving the blood flow rate data signals, the infusate flow rate data signals, the drained fluid flow rate data signals, and the patient parameter data signals, said supervisory controller analyzing said signals utilizing fuzzy logic having at least one predetermined supervisory rule, and said supervisory controller then providing an output signal to one or more of said first, second and third pumps to adjust, as necessary on a periodic ongoing basis, the flow rate of fluid generated by the one or more of said first, second and third pumps for regulating fluid removal from the patient's blood.

* * * * *

UNITED STATES PATENT AND TRADEMARK OFFICE
CERTIFICATE OF CORRECTION

PATENT NO. : 6,780,322 B1
DATED : August 17, 2004
INVENTOR(S) : John J. Bissler et al.

It is certified that error appears in the above-identified patent and that said Letters Patent is hereby corrected as shown below:

<u>Title page,</u>
Item [56], References Cited, OTHER PUBLICATIONS, "L.W. Henderson, et al." reference, change "modallty" to -- modality --.
"International Electrotechnical Commission" reference, change "requirement" to -- requirements --.
"N.J. Olsthun" reference, change "Olsthun" to -- Ofsthun --.
"J. Schaeffer, et al." reference, change "Lon" to -- Long --.
"K.S. Tsakalis, et al." reference, change "Prentic" to -- Prentice --.
"P. Kramer" reference, change "arterioverious" to -- arteriovenous --.

<u>Column 1,</u>
Line 31, after the word "patient" add -- . --.
Line 37, after the word "general", add -- , --.

<u>Column 3,</u>
Line 14, change "tern" to -- term --.
Line 50, change "patent" to -- patient --.

<u>Column 4,</u>
Line 63, after the word "weight", add -- , --.

<u>Column 7,</u>
Line 46, change "Figure" to -- Figures --.

<u>Column 10,</u>
Line 4, change "refereed" to -- referred --.

<u>Column 11,</u>
Line 41, change "wanner" to -- warmer --.

<u>Column 16,</u>
Line 12, change "volts" to -- volt --.

<u>Column 17,</u>
Line 49, after the word "patient" add -- . --.

<u>Column 18,</u>
Line 2, change "Supervisor" to -- Supervisory --.

<u>Column 20,</u>
Line 12, delete "f" and add the word -- fuzzy --.

UNITED STATES PATENT AND TRADEMARK OFFICE
CERTIFICATE OF CORRECTION

PATENT NO. : 6,780,322 B1
DATED : August 17, 2004
INVENTOR(S) : John J. Bissler et al.

It is certified that error appears in the above-identified patent and that said Letters Patent is hereby corrected as shown below:

Column 22,
Line 60, before the number "345", add -- ( --; before the number "341", add -- ( --.

Column 23,
Line 47, delete "FISC" and add -- FSIC --.

Column 25,
Line 4, delete the word "and."
Line 9, before "said", add -- and --; add a carriage return/line feed after the word "and"; and after "said", add -- at --.

Column 28,
Line 4, change the ";" to a -- : -- and double indent three following subparagraphs.
Line 9, delete "fist" and add -- first --.
Line 27, after "pump", add -- and --.
Line 60, delete "firm" and add -- from --.

Column 29,
Line 19, after "said", add -- at --.
Line 37, delete "re" and add -- rate --.

Column 30,
Line 22, after "said", add -- at --.

Signed and Sealed this

Twenty-fourth Day of May, 2005

JON W. DUDAS
*Director of the United States Patent and Trademark Office*